US008383084B2

(12) United States Patent
Tarasenko

(10) Patent No.: US 8,383,084 B2
(45) Date of Patent: Feb. 26, 2013

(54) DESTRUCTION OF SPORES THROUGH GLYCOCONJUGATE ENHANCED PHAGOCYTOSIS

(76) Inventor: Olga Tarasenko, Little Rock, AR (US)

( * ) Notice: Subject to any disclaimer, the term of this patent is extended or adjusted under 35 U.S.C. 154(b) by 892 days.

(21) Appl. No.: 11/709,369

(22) Filed: Feb. 22, 2007

(65) Prior Publication Data

US 2008/0213316 A1 Sep. 4, 2008

Related U.S. Application Data

(60) Provisional application No. 60/775,583, filed on Feb. 22, 2006.

(51) Int. Cl.
*A61K 49/00* (2006.01)
*A61K 39/02* (2006.01)
*A61K 45/00* (2006.01)

(52) U.S. Cl. .... 424/9.2; 424/9.1; 424/184.1; 424/234.1; 424/239.1; 424/246.1; 424/247.1; 424/278.1

(58) Field of Classification Search .................. 424/9.1, 424/9.2, 184.1, 234.1, 239.1, 246.1, 247.1, 424/278.1
See application file for complete search history.

(56) References Cited

PUBLICATIONS

Carmago, MM, et al. The Journal of Immunology, vol. 159, pp. 6131-6139, 1997.*
Black J. G., "Microbiology: Principles and Explorations," Sixth Edition, John Wiley & Sons, Inc. Publishing, pp. 450-453 (2005).
Kelleher, M. et al., "Identification of a Microphage-Binding Determinant of Lipophosphoglycan from Leishmania Major Promastigotes," *Proceedings of the National Academy of Sciences*, vol. 89, pp. 6-10 (1992) (Abstract).
Koenigsknecht, J. et al., "Microglial Phagocytosis of Fibrillar Beta-Amyloid Through a Betal Integrin-Dependent Mechanism," *J. Neurosci.*, vol. 24, pp. 9838-9846 (2004).
Patel, M. et al., "The Cytoplasmic Domain of the Low Density Lipoprotein (LDL) Receptor-Related Protein, But Not That of the LDL Receptor, Triggers Phagocytosis." *J. Biol. Chem.*, vol. 275, pp. 44799-44807 (2003).
Philips, M.L. et al., "ELAM-1 Mediates Cell Adhesion by Recognition of a Carbohydrate Ligand, Sialyl-Lex.," *Science*, vol. 250, pp. 1130-1132 (1990).
Pilsczek, F. et al., "Phgocytosis of *Salmonella montevideo* by Human Neutrophils: Immune Adherence Increases Phagocytosis, whereas the Bacterial Surface Determines the Route of Intracellular Processing," *Journal of Infectious Diseases*, vol. 192, pp. 200-209 (2005).
Rajagopalan, P. et al., "Direct Activation of Human Monocyte-Derived Macrophages by a Bacterial Glycoprotein Extract Inhibits the intracellular Multiplication of Virulent *Legionella pneumophila* Serogroup 1.," *Infect Immun.*, vol. 55, No. 9, pp. 2234-2239 (1987).
Rotrosen, D. et al., "Disorders of Phagocyte Function," *Annu. Rev. Immunol.*, vol. 5, pp. 127-150 (1987).
Schmidt, R., "New Approaches to Glycoconjugate Synthesis," *Pure & Appl. Chem.*, vol. 70, No. 2, pp. 397-402 (1998).
Shamash, S. et al., "The Cytokine Network of Wallerian Degeneration: Tumor Necrosis Factor-α, Interleukin-1α, and Interleukin-1β," *The Journal of Neuroscience*, Apr. 15, 2002, 22(8):3052-3060.
Witting, A. et al., "Phagocytic Clearance of Apoptotic Neuron by Microglia/Brain Macrophages in Vitro," *Journal of Neurochemistry*, vol. 75, p. 1060 (2000) (Abstract).
Tarasenko, O., et al. "Glycoconjugates for the recognition of *Bacillus* spores." Carbohydrate Research, 2004, vol. 339, pates 2859-2870.

* cited by examiner

*Primary Examiner* — Rodney P. Swartz

(57) ABSTRACT

Methods for enhancing destruction and killing of bacterial spores via phagocytosis, where phagocytosis of bacterial spores is enhanced by using a glycoconjugate. In one embodiment, the method includes the steps of modifying a surface of a bacterial spore to increase adherence to a phagocyte; and ingesting the adherence-increased spore with the phagocyte, thereby destructing and killing the spore by blocking spore-induced phagocyte cell death, while increasing phagocyte activation level and production of antimicrobial and cytocidal agents such as NO and inflammatory cytokines. The adherence of spore to a phagocyte is increased after the surface thereof is coated with a glycoconjugate to form a glycoconjugate-coated spores. The glycoconjugate-coated spores also increase ingestion of the spores by phagocytes and facilitate phagosome-lysosome fusion, which in turn results in destruction and killing of bacterial spores via phagocytosis. The method enhances adherence, ingestion, destruction and killing of bacterial spores via phagocytes, which otherwise may be resistant to phagocytosis.

38 Claims, 15 Drawing Sheets

DESTRUCTION OF SPORES THROUGH GLYCOCONJUGATE ENHANCED PHAGOCYTOSIS

CROSS-REFERENCE TO RELATED PATENT APPLICATION

This application claims the benefit, pursuant to 35 U.S.C. §119(e), of U.S. provisional patent application Ser. No. 60/775,583 filed Feb. 22, 2006, entitled "DESTRUCTION OF SPORES THROUGH GLYCOCONJUGATE ENHANCED PHAGOCYTOSIS" by Olga Tarasenko, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [7] represents the 7th reference cited in the reference list, namely, Koenigsknecht, J. and G. Landreth, Microglial phagocytosis of fibrillar beta-amyloid through a betal integrin-dependent mechanism, J. Neurosci. 2004; 24:9838-9846.

FIELD OF THE INVENTION

The present invention generally relates to phagocytic clearance of spores. More particularly, the present invention relates to compounds and methods for enhancing phagocytosis and killing of spores by blocking spore-induced phagocyte cell death, while increasing phagocyte activation level and production of antimicrobial and cytocidal agents such as nitric oxide (NO) and inflammatory cytokines.

BACKGROUND OF THE INVENTION

Spores are dormant alternate life forms produced by the genus *Bacillus*, the genus *Clostridium*, and several other genera of bacteria including *Desulfotomaculum, Sporosarcina, Sporolactobacillus, Oscillospira*, and *Thermoactinomyces*. *Bacillus* species are obligate aerobes that live in soil while *Clostridium* species are obligate anaerobes often found as normal flora of the gastrointestinal tract. The spore is not a reproductive structure but rather a resistant, dormant survival form of the organism.

Spore consists of multiple layers of resistant coats (including a cortex, a spore coat, and sometimes an exosporium) surrounding a nucleoid, some ribosomes, RNA molecules, and enzymes. Bacterial spores are resistant to antibiotics, most disinfectants, and physical agents such as radiation, boiling, and drying. The impermeability of the spore coat is thought to be responsible for the spore's resistance to chemicals. Spores can survive possibly thousands of years until a variety of environmental stimuli trigger germination, allowing outgrowth of a single vegetative bacterium in animals.

Although harmless themselves until they germinate, spores are involved in the transmission of some diseases to humans. Infections transmitted to humans by spores include anthrax, caused by *Bacillus anthracis*; tetanus, caused by *Clostridium tetani*; botulism, caused by *Clostridium botulinum*; and gas gangrene, caused by *Clostridium perfringens*.

*Bacillus anthracis* is a spore-forming, gram-positive, soil-borne organism that causes disease in both animals and humans. Human disease presents in three forms: cutaneous, gastrointestinal, and inhalational anthrax. Unless antibiotics are administered early, inhalational anthrax is associated with a high mortality rate. The inhalational form of anthrax has become a major concern because of the potential for *B. anthracis* to be used in the aerosolized form as a bioweapon.

During the very early stages of inhalation anthrax, alveolar macrophages engulf inhaled spores and transport them to the regional lymph nodes. The spores germinate within the macrophages followed by growth of the vegetative bacilli and their release into circulation, where they are capable of replicating to a density of $10^8$ CFU/ml.

*B. anthracis* is perhaps the most feared of all potential bacterial bioweapons. In inhalational anthrax, alveolar macrophages are believed to be the primary site for germination of *B. anthracis* spores. The ability of the bacteria to survive and grow within and to escape from this environment is thought to be critical for the disease to proceed.

Glycans and glycoconjugates have been shown to have numerous biological activities e.g. cell adhesion, cell-cell interactions, pathogen-host interactions, toxins in cancer and inflammation processes. Numerous pathogens use carbohydrate related interactions to gain entry into their hosts. For instance, bacteria and intestinal parasites, such as amoeba, mediate the sugar specific adherence of the organisms to epithelial cells and thus facilitate infection [1]. Numerous parasites and other infectious diseases synthesize glycans binding proteins for attachment and invasion of host cells. These parasites include helminths, *ascaris*, hookworms, malaria, amoeba, intestinal and genital flaggellates [2-4]. Furthermore, the differential expression of glycan binding molecules on the cell surfaces of organisms are correlated with pathogenicity and/or host specificity. Providing methods for delineating the interactions of surface carbohydrates between host cell and pathogen would provide useful information on understanding the biology and developing therapeutic strategies.

Therefore, a heretofore unaddressed need exists in the art to address the aforementioned deficiencies and inadequacies.

SUMMARY OF THE INVENTION

The present invention, in one aspect, relates to a method of enhancing phagocytosis by utilizing the interactions of surface carbohydrates between phagocytes and bacterial spores so as to result in destruction and killing of the bacterial spores through phagocytosis, phagocyte activation, and production of antimicrobial and cytocidal agents.

In one embodiment, the method of destructing and killing a spore produced by a bacterium includes the steps of (1) modifying a surface of the spore to increase adherence to a phagocyte, (2) activating of phagocytic cells, (3) ingesting the adherence-increased spore with the phagocyte, thereby destructing and killing the spore by blocking spore-induced phagocyte cell death, and (4) increasing phagocyte activation level and production of antimicrobial and cytocidal agents such as NO and inflammatory cytokines. The method of the invention is also applicable to treat bacterial spores present in a body of a human or a non-human animal having been exposed to the spores. In one embodiment, the method of destructing and killing a spore produced by a bacterium includes the steps of (1) modifying a surface of the spore to increase adherence to a phagocyte, (2) activating of phagocytic cells, (3) ingesting the adherence-increased spore with the phagocyte, thereby destructing and killing the spore by blocking spore-induced phagocyte cell death, and (4) increasing phagocyte activation level and production of antimicrobial and cytocidal agents such as NO and inflammatory cytokines.

Preferably, the step of modifying a surface of the spore is performed on a human or non-human animal at an early stage of infection by the spore. More preferably, the spore is present in an extracellular space or in tissue fluid in the body of the human or the non-human animal.

The step of modifying the surface of the spore includes treating the spore with an effective amount of a glycoconjugate to form a glycoconjugate-coated spore. Preferably, the glycoconjugate is immunogenic. More preferably, the glycoconjugate is capable of increasing activation of the phagocyte and adherence of the spore to the phagocyte, thereby resulting in ingestion of the glycoconjugate-coated spore and formation of a phagosome in the phagocyte. Still more preferably, the glycoconjugate facilitates phagosome-lysosome fusion in the phagocyte and produce antimicrobial agents by activated phagocytes that promote the killing of *Bacillus* spores by blocking spore-induced phagocyte cell death, while increasing phagocyte activation level and production of antimicrobial and cytocidal agents such as NO and inflammatory cytokines.

In one embodiment, the glycoconjugate is selected from the group consisting of glycan, glycoprotein, glycolipid, and any combinations thereof. Preferably, the glycoconjugate is carbohydrate units covalently linked with other types of chemical constituent. More preferably, the glycoconjugate is selected from the group consisting of Galβ1-3GalNAcα-PAA-flu, Galβ1-3GalNAcβ-PAA-flu, Fucα1-3GlcNAcβ-PAA-flu, Fucα1-4GlcNAc-PAA-flu, Fucβ1-3GlcNAcβ-PAA-flu, Galβ1-4GalNAcα-PAA-flu, Galβ1-4Glcβ-PAA-flu, GalNAcα1-3GalNAcβ-PAA-flu, GalNAcα1-3GalNAcα-PAA-flu, GlcNAcβ1-3Galβ-PAA-flu, GlcNAcβ1-4GlcNAcβ-PAA-flu, Galα1-4GlcNAcβ-PAA-flu-PAA-flu, GalNAcβ1-3GalNAcβ-PAA-flu, Glcα1-4Glcβ-PAA-flu, Galα1-2Galβ-PAA-flu, Neu5Acα2-6GalNAcα-PAA-flu, Galα1-6Glcβ-PAA-flu, Galβ1-2Galβ-PAA-flu, Neu5Acα2-3Gal-PAA-flu, Neu5Acα2-6Galβ-PAA-flu, Neu5Gcα2-6GalNAcα-PAA-flu, Neu5Acβ2-6GalNAcα-PAA-flu, Neu5Acα2-3GalNAcα-PAA-flu as a single compound. Still more preferably, the glycoconjugate is a combination thereof.

The phagocyte used in the method of the present invention may be selected from the group consisting of monocyte, macrophage, neutrophil and amoeba. Preferably, the phagocyte is a macrophage or a monocyte or a neutrophil leukocyte.

The method of the invention may be used to destruct and kill spores produced by a bacterium that is selected from the group consisting of the genus *Clostridium* and the genus *Bacillus*. In one embodiment, the bacterium is selected from the group consisting of *Bacillus cereus* and *Bacillus anthracis*.

In one aspect, the invention relates to a method of enhancing phagocytosis of spores produced by a bacterium, in which the spores is present in a body of a human or a non-human animal having been exposed to the spores, the method including subjecting the spores to an effective amount of a glycoconjugate to form glycoconjugate-coated spores, thereby increasing the activation phagocyte and phagocytosis of the glycoconjugate-coated spores by a phagocyte as compared to that of uncoated spores.

Another aspect of the invention relates to a method of removing environmental contaminations by bacterial spores, the method includes treating the spores with an effective amount of a glycoconjugate to form glycoconjugate-coated spores, and providing a phagocyte to ingest the glycoconjugate-coated spores, thereby destructing and killing the spores as a result of killing of *Bacillus* spores by blocking spore-induced phagocyte cell death, while increasing phagocyte activation level and production of antimicrobial and cytocidal agents such as NO and inflammatory cytokines. Preferably, the phagocytes is an ameba. More preferably, the phagocyte is an ameba *Dictyostelium discoideum.*

In another embodiment, the present invention relates to a method of enhancing phagocytosis of spores produced by a bacterium, the method including subjecting the spores to an effective amount of a glycoconjugate to form glycoconjugate-coated spores, thereby increasing the phagocytosis of the glycoconjugate-coated spores by a phagocyte as compared to that of uncoated spores. The method may further include a step of increasing activation of the phagocyte and adherence of the phagocyte to the glycoconjugate-coated spores to, thereby increasing the ingestion of the glycoconjugate-coated spores and resulting in increased formation of phagosome and the production of antimicrobial agent and as compared to that of uncoated spores. Preferably, the method further includes the step of increasing phagosome-lysosome fusion in the phagocyte, thereby increasing destruction and killing of the spores by the activated phagocytes.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 3A shows GSCs adhering to the cell surface; FIG. 3B shows ingestion of GCSs; FIG. 3C shows GCSs destroyed by lysosomes; and FIG. 3D shows formation of a phagolysosome.

In FIG. 5D, these results were expressed as mean percent bacterial killing of untreated spores and spores treated with glycoconjugates GC1 and GC3. These results are representative of triplicate experiments.

DETAILED DESCRIPTION OF THE INVENTION

Figure 1:
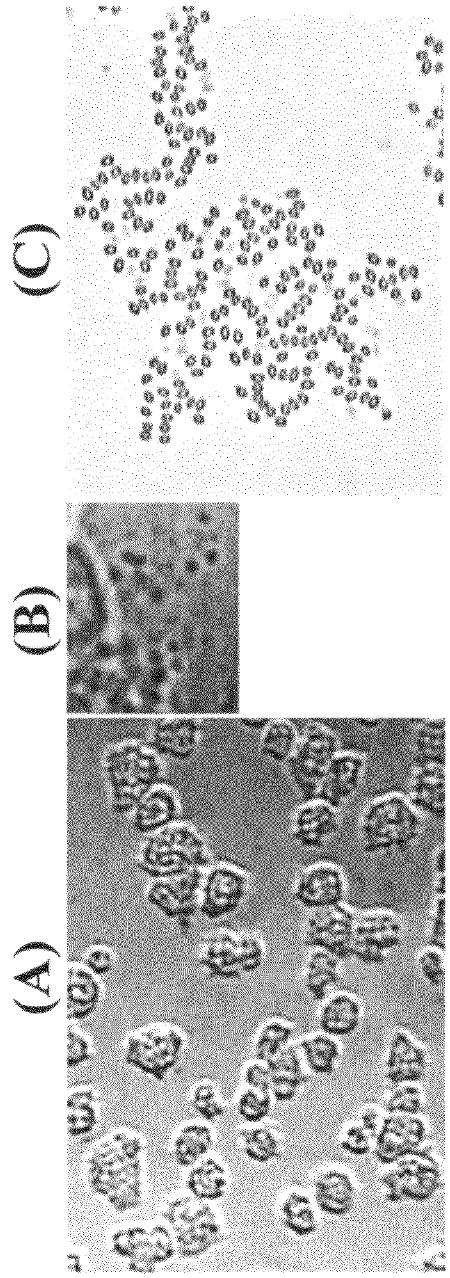
FIG. 1A shows *Dictyostelium discoideum* amoebae (strain Ax4).
FIG. 1B shows the glycoconjugate-coated *Bacillus cereus* (*B. cereus*) spores, which are no longer translucent (shown as black dots).
FIG. 1C shows the uncoated *B. cereus* spores that are translucent compared to the coated spores of FIG. 1B.

The present invention is more particularly described in the following examples that are intended as illustrative only since numerous modifications and variations therein will be apparent to those skilled in the art. Various embodiments of the invention are now described in detail. Referring to the drawings FIGS. 1-4, like numbers indicate like components throughout the views. As used in the description herein and throughout the claims that follow, the meaning of “a”, “an”, and “the” includes plural reference unless the context clearly dictates otherwise. Also, as used in the description herein and throughout the claims that follow, the meaning of “in” includes “in” and “on” unless the context clearly dictates otherwise. Moreover, titles or subtitles may be used in the specification for the convenience of a reader, which shall have no influence on the scope of the present invention. Additionally, some terms used in the specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification. The usage of subtitles, however, has no influence on the scope of the invention.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "endospores" and "spores" are interchangeable. Spores mean structures of a dormant stage of some bacteria.

As used herein, the term "phagocyte" means a cell that ingests and destroys foreign matter such as microorganisms or debris via a process known as phagocytosis, in which these cells ingest and kill offending cells by a process analogous to cellular digestion, usually using lysosomes which carry potent enzymes that digests cell components such as other lipids or proteins.

As used herein, the term "phagocytosis" means a form of endocytosis wherein large particles are enveloped by the cell membrane of a (usually larger) cell and internalized to form a phagosome, or "food vacuole." The resulting phagosome may be merged with lysosomes containing digestive enzymes, forming a phagolysosome. The food particles will then be digested, and the released nutrients diffused or transported into the cytosol to use in other metabolic processes.

As used herein, the term "oligosaccharide" means a carbohydrate compound made up of a small number of monosaccharide units. Oligosaccharides may be formed by cleaving polysaccharides.

As used herein, the term "polysaccharide" means a carbohydrate compound containing a large number of saccharide groups.

As used herein, the term "immunogenic" means causing an immune response.

As used herein, the abbreviation "Gal" means galactosyl.

As used herein, the abbreviation "GalNAc" means N-acetyl-galactosamine.

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated RNA, DNA, or a restriction fragment, or polymers. Isolated nucleic acid molecules also include, for example, sequences inserted into plasmids, cosmids, artificial chromosomes, and the like. An isolated protein may be associated with other proteins or nucleic acids, or both, with which it associates in the cell, or with cellular membranes if it is a membrane-associated protein. Isolated macrophages include, for example, murine macrophages or human macrophages from peripheral blood.

As used herein, the term "genetic similarity" or "genetically identical" refers to a polypeptide or nucleic acid molecule exhibiting at least 80%, more preferably at least 90%, and most preferably at least 95% identity in comparison to a reference amino acid or nucleic acid sequence. For polypeptides, the length of sequence comparison will generally be at least 20 amino acids, preferably at least 30 amino acids, more preferably at least 40 amino acids, and most preferably at least 50 amino acids. For nucleic acid molecules, the length of sequence comparison will generally be at least 60 nucleotides, preferably at least 90 nucleotides, and more preferably at least 120 nucleotides. The degree of sequence identity between any two nucleic acid molecules or two polypeptides may be determined by sequence comparison and multiple sequence alignment algorithms known in the art, including but not limited to BLAST, FASTA, DNA Strider, and the GCG Package (Madison, Wis.) pileup program.

As used herein, the term "host cell" refers to a cell of the "subject" which has been used for immunomodulation with one or more compounds of the invention. Exemplary host cells include murine and mammalian macrophages and or other peripheral blood mononuclear cells.

As used herein, the term "gene" refers to a DNA sequence that codes for or corresponds to a particular sequence of amino acids which comprise all or part of one or more polypeptides, and may or may not include regulatory DNA sequences (e.g., promoter sequences), which determine, for example, the conditions under which the gene is expressed.

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

As used herein, the term "effective amount" means sufficient compound compositions that administer, prevent cell death, and elicits immune response. One skilled in the art recognizes that this level may vary.

As used herein, the term "subjects" means mammals, particularly domesticated livestock including but not limited to dogs, cats, cows, bulls, steers, pigs, horses, sheep, goats, mules, donkeys, and the like, that have been exposed to or infected with, or are at risk of being exposed to or infected with, *B. anthracis* or *B. anthracis* spores. Most preferably, a subject is a human.

As used herein, the term "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. The host may be a mammal, preferably a human.

As used herein, the term “LC50: (Lethal Concentration 50)” is the concentration of a chemical and/or compound which kills 50% of a sample population such as bacterial spores when administered as a single exposure (typically 1 or 4 hours). Also called the median lethal concentration and lethal concentration 50, this value conveys the relative acute toxicity of material. This measure is generally used when exposure to a chemical is through the subject breathing it in.

As used herein, the term “LD50 (Lethal Dose 50)” is the dose of a toxicant or microbe that will kill 50 percent of the test organisms within a designated period. The lower the LD 50, the more toxic is the compound. The LD50 is the measure generally used when exposure is by swallowing, through skin contact, or by injection.

The term “therapeutically effective amount” is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. The host may be a mammal, preferably a human.

As used herein, the phrase “pharmaceutically acceptable” refers to molecular entities and compositions that are “generally regarded as safe”, e.g., that are physiologically tolerable and do not typically produce an allergic or similar untoward reaction, such as gastric upset, dizziness and the like, when administered to a human. Preferably, as used herein, the term “pharmaceutically acceptable” means approved by a regulatory agency of the Federal or a state government or listed in the U.S. Pharmacopeia or other generally recognized pharmacopeia for use in animals, and more particularly in humans.

As used herein, the term “carrier” refers to a diluent, solvent, adjuvant, recipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavor, and a colorant. Suitable pharmaceutical carriers are described in “Remington’s Pharmaceutical Sciences” by E. W. Martin.

As used herein, the term “vaccine” refers to a composition comprising a cell or a cellular antigen, and optionally other pharmaceutically acceptable carriers, administered to stimulate an immune response in an animal, preferably a mammals, most preferably a human, specifically against the antigen and preferably to engender immunological memory that leads to mounting of a protective immune response should the subject encounter that antigen at some future time. Vaccines often comprise an adjuvant.

As used herein, the term “immunomodulation” signifies adjustment of the immune response to a desired level, as in immunopotentiation, immunosuppression, or induction of immunologic tolerance.

As used herein, the term “immunomodulator” is a drug used for its effect on the immune system. There are two types of such drugs based on their effects: immunostimulators and immunosuppressive. Immunostimulators are drugs that stimulate the immune system by inducing activation or increasing activity of any of its components. There are two main categories of immunostimulators:

Specific immunostimulators are those which provide antigenic specificity in an immune response, such as vaccines or any antigen.

Non-specific immunostimulators are those that act irrespective of antigenic specificity to augment an immune response of other antigen or stimulate components of the immune system without antigenic specificity, such as adjuvants and non-specific immunostimulators.

An immunosuppressive drug is any of a variety of substances used to prevent production of antibodies. These are commonly used to prevent rejection by a recipient’s body of an organ transplanted from a donor.

As used herein, the term “immune response” refers to the development in the host of a cellular and/or antibody-mediated immune response to a composition or vaccine of interest. Such a response usually consists of the subject activating macrophages, producing antibodies, B cells, helper T cells, suppressor T cells, and/or cytotoxic T cells, cytokines, chemokines directed specifically to an antigen or antigens included in the composition or vaccine of interest.

As used herein, the term “antigen” is a substance that, when introduced into the body, stimulates the production of an antibody. Antigens include spores, toxins, bacteria and their constituents including but not limited to proteins, RNA, DNA, foreign blood cells, and the cells of transplanted organs.

As used herein, the term “specific and non-specific immune responses” refer to Antigens (or pathogens) originate within the body or from the outside environment. The immune system provides two lines of defense: nonspecific and specific immunity. A first-time encounter with an antigen elicits a nonspecific immune response. Defense mechanisms include skin, mucous membranes, chemicals, specialized cells, and the inflammatory response. Unbroken skin is a formidable physical barrier to most antigens. Mucous membranes line body cavities such as the mouth and stomach. These structures secrete saliva and hydrochloric acid, respectively, chemicals that destroy bacteria. If antigens pass through the defenses, a variety of white blood cells such as macrophages, neutrophils, and mast cells try to destroy them. Other mechanisms in the blood such as complement (antibacterial proteins), interferon (antiviral proteins), and natural killer cells aid in the battle.

Specific immune response: Collection of several immunological events in which lymphocytes recognize the presence of a particular antigen and act to eliminate it.

Nonspecific immunity that which does not involve humoral or cell-mediated immunity, but includes lysozyme and interferon activity, etc. For instance The B lymphocytes are associated with humoral response and the T lymphocytes are associated with the cell-mediated response. Macrophages, heterophils and thrombocytes are the main cells associated with the nonspecific immune system.

As used herein, the term “primary and secondary immune response” refers to a response to an agent against which the body has already formed memory cells is called a secondary response. All other responses are primary responses.

As used herein, the term "opsonin" refers to a substance that enhances the phagocytosis of bacteria by leukocytes. A term used in serology and immunology Opsonin is generally synonymous with the bacteriotropin of F. Neufeld and coworkers (1904-1905), a relatively thermostable antibody, increased in amount during specific immunization that renders the corresponding bacterium more susceptible to phagocytosis. There is evidence that this action can be promoted to some extent by antibody alone, but that it is substantially increased by the further addition of the thermo-labile complement system.

An opsonin is an antibody or product of complement activation in blood serum that causes bacteria or other foreign cells to become more susceptible to the action of phagocytes. An opsonin is any molecule that acts as a binding enhancer for the process of phagocytosis, for example, by coating the negatively-charged molecules on the membrane. Both the membrane of a phagocytizing cell, as well as its target, have a negative charge (Zeta-potential), making it difficult for the two cells to come close together.

As used herein, the term "opsonization" refers to the process during which antigens are bound by antibody and/or complement molecules. Phagocytic cells express receptors that bind opsonin molecules. With the antigen coated in these molecules, binding of the antigen to the phagocyte is greatly enhanced. Most phagocytic binding cannot occur without opsonization of the antigen.

Furthermore, opsonization of the antigen and subsequent binding to an activated phagocyte will cause increased expression of complement receptors on neighboring phagocytes. Examples of opsonin molecules include the IgG antibody and the C3b, C4b, and iC3b components of the complement system.

As used herein, the term "disease" or "medical condition" is an abnormality of the body or mind that causes discomfort, dysfunction, distress, or death to the person afflicted or those in contact with the person. Sometimes the term is used broadly to include injuries, disabilities, disorders, syndromes, infections, symptoms, deviant behaviors, and atypical variations of structure and function, while in other contexts these may be considered distinguishable categories. In the narrow sense, a disease is the invasion of the body by pathogens.

As used herein, the term "adjuvant' refers to a compound or mixture that enhances the immune response to an antigen. An adjuvant can serve as a tissue depot that slowly releases the antigen and also as a lymphoid system activator that non-specifically enhances the immune response (Hood et al., Immunology, Second Ed., 1984, Benjamin/Cummings: Menlo Park, Calif., p. 384). Often, a primary challenge with an antigen alone, in the absence of an adjuvant, will fail to elicit a humoral or cellular immune response.

As used herein, the term "monomer", as used herein, refers to both a molecule comprising one or more polymerizable functional groups prior to polymerization, and a repeat unit of a polymer. A copolymer is said to be characterized by the presence of two or more different monomers.

As used herein, the term "polymer backbone" or "backbone" refers to that portion of the polymer that consists of a continuous chain comprising the bonds which are formed between monomers upon polymerization. The composition of the polymer backbone can be described in terms of the identity of the monomers from which it is formed, regardless of the composition of branches, or side chains, off of the polymer backbone. Thus, poly(acrylic acid) is said to have a poly(ethylene) backbone which is substituted with carboxylic acid (—C(O)OH) groups as side chains.

As used herein, the term "binding", used with respect to a species of sporeforming pathogens, refers to a condition in which the species are attached to a conjugate(s) with an attractive force stronger than attractive forces that are present in the intended environment of use of the surface, and that act on the species. Binding may, e.g., mean covalent interactions or bonds, ionic interactions or bonds, hydrogen bonds, hydrophobic interactions and the like.

As used herein, the term "biomolecule" refers to all molecules of biological origin, be they natural (i.e. sporeforming bacteria or fungi) or engineered. This also includes synthetic or artificial molecules that have biological like characteristics using nanotechnology, biotechnology and the like.

As used herein, the term "target" in this context refers to a agent/pathogen including but not limited to bacterial and fungi spores, which is the object of attempted binding, inhibition and inactivation.

The term "sporeforming agents" refers to spores including pathogens infectious to humans, pathogens infectious to animals, pathogens infectious to herbs/plants/trees, pathogens occur in water, soil, food, beverages and any other objects and/or articles that can be infected and/or colonized.

As used herein, the term "glycan" refers to any saccharide or oligosaccharide, in free form or attached to another molecule and that can be hydrolyzed into these units.

As used herein, the term "glycoconjugate" may be used for any molecule which contains a carbohydrate moiety (which is glycosylated), like glycoproteins or glycolipids. "Glycoconjugate" also refers to any natural or non-natural non-carbohydrate compounds that mimic the physical, structural and chemical characteristics including the biological activities of natural or engineered functions of saccharides, and any combinations thereof. The term "glycoconjugate" also refers to a molecule comprised of a glycan moiety and possibly a non-glycan moiety, such that the interaction between the glycan and non-glycan moiety is sufficiently strong so as not to be released during the binding or inhibition unless this is done by design. In this context the term "non-glycan" moiety refers to any molecule of natural and non-natural origin including: naturally occurring macromolecules such as: proteins, lipids, RNA, DNA, biopolymers and the non-natural macromolecules with biological-like feature(s) produced using man-made engineering and fabrication design principles such as nano-injection molding or stamping, molecular imprinting or templating, as well as sequential-reaction based nanomaterials such as dendrimers, molecular rosettes, star-fish and the like.

As used herein, the terms "glycan" and "glycoconjugate" are used interchangeably herein. In this context, an "oligosaccharide" is defined as a branched or linear chain of monosaccharides attached to one another via glycosidic linkage.

As used herein, the term "monosaccharide" is defined herein as a carbohydrate that cannot be hydrolyzed into a simpler unit. A monosaccharide can be of two types containing a carbonyl at the end of the carbon chain, termed an aldolase, or at the inner carbon, termed a ketose. Common animal monosaccharides include for example:

Sialic acids: a family of nine-carbon acidic sugars the most common of which is N-acetyl neuraminic acid Hexoses: six carbon neutral sugars, such as glucose, galactose and mannose.

Hexosamines: Hexose with an amino group at the 2-position, which can be either free or, more commonly, N-acetylated; N-acetylglucosamine, and N-acetylgalactosamine.

Deoxyhexoses: six-carbon neutral sugars without the hydroxyl group at the $6^{th}$ position, for example, fructose.

Pentoses: Five-carbon sugars such as xylose.

Uronic acids: Hexose with a negatively charged carboxylate at the 6-position such as glucuronic acid and iduronic acid.

These monosaccharides dominate eukaryotic glycobiology, but numerous variants can be found in lower organisms some of which are involved in numerous disease states.

The term "glycome" refers to all glycans expressed in a cell and represents the next level of increasing biological complexity. This is due to the fact that the chemical structure of the monosaccharide bond allows two possible linkages and the formation of branched structures, as opposed to nucleotides and proteins which form only linear polymers and have only one basic type of linkage. As a result, the structural complexity of glycans is several orders of magnitude greater than proteins and DNA.

As used herein, the term "binding" refers to any molecule that can undergo biological binding with a particular biological molecule. The term "binding region" refers to an area of a binding partner that recognizes a corresponding biological molecule and that facilitates biological binding with the molecule, and also refers to the corresponding region on the biological molecule. Binding regions are typified by nucleotides, molecular domains that promote van der Waals interactions, areas of corresponding molecules that interact physically as a molecular "lock and key", and the like.

Anthrax deadly disease: Anthrax is a deadly disease caused by *Bacillus anthracis*. Controlling *B. anthracis* species is important because they can be used as potential biological warfare agents, and bioterrorism. Additionally, *Bacilli* are responsible for food spoilage and food-borne illness problems. Effective prevention and treatment of anthrax cannot be achieved over a broad area when mass exposures occur. This problem would intensify significantly if military forces and/or the general population are exposed to weaponized, genetically-engineered bacteria or bacterial spores.

*B. anthracis* has been placed within the *B. cereus* group due to genetic similarities. About 426 *B. anthracis* strains have been isolated worldwide. Non-virulent *B. anthracis* cannot be unambiguously discerned from other *B. cereus* strains. The virulence of anthrax is determined by the pathogen's escape from macrophages, multiplication, toxins release, and causing apoptosis. *Bacillus* spores enter the body through the skin, lungs, or the gastrointestinal tract and are engulfed by macrophages, which may carry them to local lymph nodes. Once spores germinate, the vegetative cells produce powerful toxins that diminish macrophage capacity to kill the bacteria. *B. anthracis* vegetative cells divide, are disseminated through the blood stream and produce toxins such as edema factor (EF) and lethal factor (LF), which along with protective antigen (PA), reduce host resistance to infection. Cellular internalization of EF and LF causes clinical symptoms of an anthrax infection.

Anthrax vaccination and treatment: Effective prevention and treatment of anthrax remains elusive due to the limitations of current vaccines and anti-bacterial agents. Anthrax PA appears to be the main component of all existing anthrax vaccines. Unfortunately, only a few strains were used in the vaccine preparation. The U.S. vaccine (AVA Biothrax, also known as AVA or MDPH-PA) is prepared from the virulent *B. anthracis* V770-NP1-R strain. The vaccine developed in the UK is prepared from the filtered *B. anthracis* 34F2 Sterne strain. Antibodies induced by anthrax vaccines recognize PA, blocking the binding and internalization of EF and LF. Specificity and selectivity of antibodies depend on antigen-binding regions and antigen and their corresponding bacterial spore receptor structures. Changes of antigens can render antibodies ineffective. Post-vaccination host immune response will develop on the $15^{th}$ day of urgent immunization but symptoms of anthrax infection usually develop only after 4-5 days after exposure.

Investigators have reported limitations with the current, licensed vaccines. The vaccine imposes serious adverse reactions on the nervous system, skin, and tissue and may cause muscular-skeletal disorders, anaphylaxis, and/or serious local allergic reactions. Furthermore, the PA-specific response to the UK vaccine peaks two weeks post-immunization and declines to pre-boost levels by the $12^{th}$ week. In addition, the PA-specific antibody response varies widely with host heterogeneity. PA and their anti-apoptotic effects on cells were not investigated. Although available anthrax vaccines can prevent classical anthrax, genetic mixing of different resistant *B. anthracis* strains, or even modification of non-virulent bacterial species, can render the vaccine ineffective.

The preferred drugs for anthrax treatment are penicillin, ciprofloxacin, and doxycycline. However, antibiotic resistance due to a high bacterial mutation rate has life-threatening consequences. There is a need for a new effective vaccine, drugs and/or immunomodulators that decrease morbidity and mortality associated with infections caused by spores, their vegetative cells and toxins.

Glycoconjugates and their applications: Both mammalian and bacterial cells express complex glycoconjugate structures, including glycoproteins, glycolipids, glycosaminoglycans, and proteoglycans. Glycoconjugates are involved in cell recognition and signaling processes intrinsic to biochemical functions in cells. Carbohydrates are recognized as differentiation markers of cells and antigenic determinants. Carbohydrates play a central role in cell-to-cell adhesion and in subsequent recognition and receptor activation. The potential use of glycoconjugates for biomedical and pharmaceutical applications is due to the fact that glycoconjugates can be designed to meet specific physicochemical requirements and have a long shelf-life and low toxicity.

Anthrax can be attenuated if macrophages will be activated in order to kill anthrax spores. Among potential cellular targets by glycoconjugates, phagocyte cells including but not limited to macrophages are considered ideal, since they play a central role in inflammation and innate immunity to microorganisms involved with infectious diseases. We previously reported that glycoconjugates contributed to the recognition, inhibition, and destruction of bacterial spores. Furthermore, the glycoconjugates promote the recognition and inhibition of spores and their vegetative cells and toxins, activate macrophages, enhance phagocytosis of spores achieved by macrophages, prevent macrophage cell death, and kill bacterial spores.

Phagocytosis and their mechanisms: Phagocytosis is an essential mechanism that inflammatory leukocytes utilize in engulfing and killing or clearing pathogenic microorganisms or dead cells. It is well established that invading pathogens were initially neutralized by a battery of circulating host defensive proteins and quickly cleared from circulation or body fluid by inflammatory leukocytes via phagocytosis. The recognition and engulfing of pathogen complex is triggered by interaction with specific receptors on the leukocytes, and followed by cellular actin assembly, pseudopod extension and phagosome closure. Phagocytosis, endocytotic events sequel to binding particle ligands to the specific receptors on phagocyte cell surface such as Fcγ receptor (FcγR), complement receptor (CR), O-glucan receptor, and phosphatidylserine (PS) receptor, require actin assembly, pseudopod extension and phagosome closure. Rho GTPases (RhoA, Cdc42, and Rac1) are critically involved in these processes. Rho family GTPase proteins known to be involved in many physiological functions like rearrangement of cytoskeletons, regulation of cellular morphology, chemotaxis, and regulation of transcription, are essential in actin dynamics necessary for phagocytosis and engulfment. There are three mechanisms of phagocytosis including FcγR-, complement receptor-, and mannose receptor-mediated phagocytosis.

FcγR-mediated phagocytes: Ligands interaction with Fcγ receptor (FcγR) and complement receptors (CRs) that are linked to distinct signaling pathways, induce both morphologically and mechanistically distinct phagocytic processes. FcγR can recognize Fc domain of immunoglobulin G (IgG). FcγR that mediate phagocytosis in human macrophages include FcγRI, IIA, and FcγRIII. The human FcγRIIA is a monomeric protein which has an extracellular Fc binding domain, a transmembrane domain, and a cytoplasmic tail domain containing two immunoglobulin gene family tyrosine activation motifs (ITAMs), which is phosphorylated by tyrosine kinase of the Src family activated upon FcγR aggregation. FcγRI and FcγIIIA have also extracellular Fc binding domains similar to FcγRIIA, but lack ITAMs on their cytoplasmic tails. It was found that Cdc42/Rac regulated the phagocytosis mediated through FcγR in macrophages.

Complement receptor-mediated phagocytosis: Another receptor through which phagocytosis occurs is the CRs, which recognizes the C3b/C3bi fragments. The complement fragments are generated by cleavage of C3 to active C3b and subsequently to inactive C3b (C3bi). CR1 is thought to participate mainly in particle binding. CR3 (CD11b/CD18; Mac-1) and CR4 (CD11c/CD18) are heterodimers of integrin members, αMβ2 and αXβ2, respectively, which are responsible for particle internalization. Rho appeared to be involved in the regulation of phagocytosis that is mediated through CR3. Rho appeared to be also involved in FcγR-mediated phagocytosis. The clustering of receptors in response to opsonin, an essential step in Fcγ-induced signaling, is the earliest event to be inhibited by C3 exoenzyme. Taken together, Rho is also required for the initiation of phagocytosis by FcγRs in macrophages. Another small GTPase, constitutively active Rap 1 is sufficient for functional activation of CR3 allowing phagocytosis of C3bi-opsonized target, and inhibition of Rap1 abolishes activation of CR3 induced by phobol esters, lipopolysaccharide (LPS), tumor necrosis factor (TNF)-α or platelet activating factor (PAF). Rap1 may link the signaling through FcγR and that through CR3. IgG-coated particles induce a rapid and transient Rap1 activation. However, Rap1 is activated independently of respiratory burst induction. In turn, Rap1 activation specifically controls the binding properties of CR3 towards its physiological ligand, the complement-opsonized phagocytic target. CR3 requires additional stimuli such as phorbol 12-myristate 13-acetate (PMA), chemokines, TNF-α or adhesion to fibronectin-coated surface, which results in activation of protein kinase C(PKC) and increased expression of CR3 at the surface. In some cases, CR3 and CR4 are also involved in antibody-mediated complement-independent phagocytosis. IgM and IgA-mediated phagocytosis of *C. neoformans* is dependent on CR3 expression, and is inhibited by soluble glucuronoxylmannan (GXM), which binds CD18. Since CD18 can bind GXM, it is considered that IgM- and IgA-mediated phagocytosis reflects facilitated binding of exposed capsular polysaccharide by CR3 and CR4 as a consequence of antibody binding to capsule of microorganism.

Mannose receptor-mediated phagocytosis: The third type of receptor involved in phagocytosis is the mannose receptor that recognizes mannose and fucose saccharides in the capsule on the lipopolysaccharide of invading bacteria. Cellular recognition of nonopsonized zymosan is mediated by mannose and β-glucan receptors. Nonopsonized zymosan can be also ingested through CR3, the lectin domain of which binds to soluble β-glucan and mediates phagocytosis of particles containing β-glucan, such as zymosan. Thereby, it is proposed that CR3 be β-glucan receptor. However, it was recently reported that dectin-1 is a major β-glucan receptor on macrophages.

Post-Phagocytosis events: Subsequent to phagocytosis in macrophage, there is an abrupt increase of superoxide formation known as the oxidative burst, which is catalyzed by an NADPH oxidase enzyme complex. The NADPH oxidase is a membrane-associated enzyme complex that generates superoxide ($O_2$) by the one-electron reduction of oxygen, using NADPH as the electron donor. NADPH oxidase is composed of multiple subunits from membrane and cytosolic fractions. The core enzyme of NADPH oxidase is composed of five components. Among them, p22PHOX and gp91PHOX exist in the membranes of secretory granular vesicles that fuse with the plasma membrane upon phagocytosis, and p22 PHOX and gp91 PHOX form a heterodimeric flavohemoprotein known as cytochrome b558. The other components, p40PHOX, p47PHOX, and p67PHOX are located in the cytosol as a complex. When cells are activated, p47PHOX becomes highly phosphorylated by protein kinases, and the entire cytosolic complex of p40PHOX, p47PHOX, and p67PHOX translocates to the membrane, where it associates with cytochrome b558 to assemble the active NADPH oxidase. In addition to p40PHOX, p47PHOX, and p67PHOX, two Ras-related small GTP-binding proteins, Rap1 and Rac1 (or Rac2) are required for the activation of NADPH oxidase. Ras-related small GTP-binding proteins, Rac1 and Rac2 are essential regulators of the activation of NADPH oxidase. The cytosolic subunits and Rac-GTP are translocated to the membrane, forming complete NADPH oxidase complex with membrane part subunits. Rac2 is the major homologue found in human phagocytes, while Rac1 is the major form in mouse. In the resting state of phagocytosis, Rac is localized in the cytoplasm in a dimeric complex with Rho GDP dissociation inhibitor (GDI), while GTP-bound Rac translocates to the membrane independently of p40PHOX, p47PHOX, and p67PHOX cytosolic complex translocation during activation of the phagocyte. Rap1 physically associated with and co-purifies with cytochrome b558 in the membranes. Rap1 is phosphorylated by protein kinase A and the phosphorylated Rap1 is inhibited from binding to cytochrome b558, suggesting that a kinase(s) may regulate the interaction between cytochrome b558 and Rap1. In addition, IgG-coated particles induce a rapid and transient Rap1 activation. In neutrophil, Rap1 is activated independently of respiratory induction. The NADPH oxidase is activated on phagosomes and generates superoxide to aid in the killing of phagocytosed microorganisms. It is important that superoxide is primarily released into phagosomes to prevent damage to surrounding cells. It was proposed that PI3K/p38 MAPK/Rac pathway is operative in the activation of NADPH oxidase in neutrophils. Rac is involved in FcγR-mediated phagocytosis, and directly in the activation of NADPH oxidase. In addition, RhoA was also reported to be involved in the production of H202 in other cell lines such as Swiss 3T3 fibroblast and Rat-2 fibroblast, when stimulated by TGF and EGF, respectively. RhoA has been known as an activator for Rho-dependent protein kinase (ROK), which phosphorylates myosin light chain kinase (MLCK), and myosin binding subunit of myosin phosphatase, which results in the formation of stress fibers. Cytoskeleton reorganization is also linked to superoxide formation Inhibition of superoxide formation by cytochalasin B suggests a necessary role of the cytoskeleton in the signaling pathway that activates the oxidase. ML-7, an inhibitor of MLC kinase, inhibited superoxide formation and phagocytosis in some laboratories, suggesting that cytoskeleton reorganization is important for the superoxide formation. In addition, the inhibition of superoxide formation by ML-7 may arise from the reduction of the phagocytosis, where ML-7 will likely directly inhibits the machinery to produce superoxide: ML-7 was shown to reduce the phosphorylation and the translocation of p47PHOX to the membranes. It has been shown that p22PHOX can be phosphorylated through phospholipase D (PLD), suggesting that PLD activity is required for superoxide formation. Involvement of PLD was further evidenced by that the activation of PLD is tightly coupled to the phagocytosis of opsonized zymosan by human macrophages and RhoA is an activator of PLD activity. Interestingly, Rac/RhoGDI complex was disrupted in the presence of various lipids like arachidonic acid, phosphatidylinositol, and phosphatidic acid (PA) which can be produced by PLD. Recently it was demonstrated that RhoA is regulated by Rac through superoxide where the change in cellular redox state appeared to couple to the control of actin cytoskeleton rearrangement by Rho GTPase. Rac-mediated ROS production results in the down-regulation of Rho activity. The pathway linking generation of ROS to downregulation of Rho involves inhibition of the low-molecular weight protein tyrosine phosphatase and then an increase in the tyrosine phosphorylation and activation of its target, p190Rho-GAP.

Nitric Oxide (NO) and biological activities of NO: Endogenous nitric oxide (NO) is synthesized from the L arginine by a family of NO synthase (NOS) isoenzymes [endothelial NOS (eNOS), neuronal NOS (nNOS) and inducible NOS (iNOS)]. The NOS isoforms are denoted by descriptive terms, based on the requirement of intracellular calcium transients for full activity. NO is a small, lipophilic, diffusible, highly reactive molecule with dichotomous regulatory roles in many biological events under physiological and pathological conditions. NO is a signal molecule of key importance for the cardiovascular system and it was also found to exert a series of other functions. NO acts as a signal molecule in the nervous system, as a weapon against infections, as a regulator of blood pressure and as a gatekeeper of blood flow to different organs. NO is present in most living creatures and made by many different types of cells. When NO is produced by the innermost cell layer of the arteries, the endothelium, it rapidly spreads through the cell membranes to the underlying muscle cells. Their contraction is turned off by NO, resulting in a dilatation of the arteries. In this way, NO controls the blood pressure and its distribution. It also prevents the formation of thrombi. When NO is formed in nerve cells, it spreads rapidly in all directions, activating all cells in the vicinity. This can modulate many functions, from behavior to gastrointestinal motility.

When NO is produced in white blood cells (such as macrophages), huge quantities are achieved and become toxic to invading bacteria and parasites. It is now generally accepted that NO or related nitrogen oxides produced by activate macrophages are cytostatic or cytotoxic for a variety of pathogens, including *Leishmania major, Mycobacterium bovis, Toxoplasma gondii, Schistosoma mansoni, Cryptococcus neoformans, Trypanosoma musculi*, and *T. cruzi*. NO is generated from the terminal guanidino nitrogen atom of L-arginine by an NADP-dependent enzyme, NO synthase. In macrophages, the enzyme activity is inducible by cytokines such as IFN-γ and tumor necrosis factor alpha (TNF-α). TNF-α acts in an autocrine fashion to amplify the actual synthesis and release of NO by IFN-γ-primed macrophages.

NO can promote apoptosis (pro-apoptosis) in some cells, whereas it inhibits apoptosis (anti-apoptosis) in other cells. This complexity is a consequence of the rate of NO production and the interaction with biological molecules such as metal ion, thiol, protein tyrosine, and reactive oxygen species. Long-lasting overproduction of NO acts as a pro-apoptotic modulator, activating caspase family proteases through the release of mitochondrial cytochrome c into cytosol, up-regulation of the p53 expression, and alterations in the expression of apoptosis associated proteins, including the Bcl-2 family. However, low or physiological concentrations of NO prevent cells from apoptosis that is induced by the trophic factor withdrawal, Fas, TNFα/ActD, and LPS. The antiapoptotic mechanism is understood on the basis of gene transcription of protective proteins. These include: heat shock protein, hemeoxygenase, or cyclooxygenase-2 and direct inhibition of the apoptotic executive effectors caspase family protease by S-nitrosylation of the cysteine thiol group in their catalytic site in a cell specific way.

At the interface between the innate and adaptive immune systems lies the high-output isoform of nitric oxide synthase (NOS2 or iNOS). This remarkable molecular machine requires at least 17 binding reactions to assemble a functional dimer. Sustained catalysis results from the ability of NOS2 to attach calmodulin without dependence on elevated $Ca^{2+}$. Expression of NOS2 in macrophages is controlled by cytokines and microbial products, primarily by transcriptional induction. NOS2 has been documented in macrophages from human, horse, cow, goat, sheep, rat, mouse, and chicken. Human NOS2 is most readily observed in monocytes or macrophages from patients with infectious or inflammatory diseases. Sustained production of NO endows macrophages with cytostatic or cytotoxic activity against viruses, bacteria, fungi, protozoa, helminthes, and tumor cells. The antimicrobial and cytotoxic actions of NO are enhanced by other macrophage products such as acid, glutathione, cysteine, hydrogen peroxide, or superoxide. Although the high-output NO pathway probably evolved to protect the host from infection, suppressive effects on lymphocyte proliferation and damage to other normal host cells confer upon NOS2 the same protective/destructive duality inherent in every other major component of the immune response. Activated macrophages do not synthesize NO or display antimicrobial activity in the presence of NG-monomethyl-L-arginine (L-NMMA), Nw-nitro-L-arginine (NOARG), or L-imino-ethyl-L-ornithine (L-NIO), substrates that inhibit nitrogen oxidation of L-arginine.

Constitutive NOS (cNOS), such as eNOS and nNOS, is activated by a transitory increase generally in cytosolic calcium, which promotes the release of NO over several minutes. Akt-dependent phosphorylation and translocation to the cytoplasmic membrane can also activate eNOS. A cytokine-inducible NOS isoform is expressed in many cells including macrophages and hepatocytes after the stimulation of immunological or inflammatory reactions. This produces large amounts of NO for several days. These characteristics suggest another classification of the isoforms into low- or high-output NOS for endogenously synthesized NO. NOS inhibitors, such as N-monomethyl-L-arginine (LNMMA), are widely used to inhibit NO synthesis, thus allowing the contribution of the effects of NO on the overall response to be assessed. To know the effects of NO on the cell survival, or without the involvement of NOS, NO-releasing compounds (NO donors)

are valuable tools. They preserve NO in their molecular structure and exhibit biological activity after decomposition. These chemicals exhibit considerable variation in their structure, stability, and biological activity. Different bioavailability arises from the differences in bioactivation and enzymatic versus nonenzymatic NO release. Examples are organic nitrates, 3-morpholinosydnonimine (SIN-1), sodium nitroprusside (SNP), S-nitrosothiols (e.g. S-nitrosoglutathione) (GSNO), Snitroso-N-acetylpenicillamine-amine (SNAP), and Snitrocysteine (CysNO), as well as compounds that contain the N(O)NO-functional group, such as the diethylamine-nitric oxide compound (DEA-NO) and spermine-NO.

The biological activities of NO can be divided into cGMP-dependent and cGMP-independent pathways. NO is a transducer of the vasodilator message from the endothelium to the vascular smooth muscle. It is also a neurotransmitter in the central and peripheral nervous systems, and participates in non-specific immune responses. Even though NO can affect the cellular functions through posttranslational modifications of proteins directly (i.e. nitrosylation and nitration) and indirectly (i.e. methylation and ribosylation), the main physiological signaling pathway of NO is considered to be the activation of guanylate cyclase, formation of cGMP, and concomitant protein phosphorylation. The reactions with oxygen, superoxide, and transition metals are more relevant for understanding the cytostatic or cytotoxic signals. The reaction products—NOx, peroxynitrite (ONOO—) and metal-NO adduct, respectively support additional reactions through their interaction with targets via redox and additive chemistry. Examples of the toxic actions of NO are neurodegenerative diseases, or pancreatic β-cell destruction. Mechanistically, the diffusion limited reaction of NO with superoxide that is known to generate ONOO—, inhibition of FeS-enzymes (such as the Krebs-cycle aconitase), complexes I and II of the mitochondrial respiratory chain, or ribonucleotide reductase, deregulation of poly(APP-ribose) polymerase, and energy depletion are all reported as probable causes for cell death. Furthermore, NO can regulate apoptotic signaling cascade by the regulation of several gene expressions, mitochondrial dysfunction, and caspase activity/activation.

Cell death: apoptosis versus necrosis: Cell death is believed to occur by either necrotic or apoptotic mechanisms. These are two distinct forms of cell death, which have different defining morphological and molecular features, and implications for the surrounding tissue. Apoptosis, or programmed cell death, is a strictly regulated device that is responsible for the ordered removal of superfluous, aged, or damaged cells. Morphologically, in cells undergoing apoptosis there is ruffling, blebbing, and condensation of the plasma and nuclear membranes, and subsequently aggregation of the nuclear chromatin. Mitochondria and ribosomes retain their gross structure, and at the least, partial function. There is also disruption of the cytoskeletal architecture. The cell shrinks, and then fragments into a cluster of membrane-enclosed "apoptotic bodies" that are rapidly ingested by adjacent macrophages or other neighboring phagocytic cells. As these apoptotic bodies induce no significant cytokine release by the phagocytic cells, the process progresses without concomitant induction of an inflammatory response. Apoptotic cells display a characteristic fragmentation pattern of DNA into distinct segments that can be visualized as a ladder of bands by gel electrophoresis. However, the DNA ladder formation is not ultimately required or causatively linked to the death process. Apoptosis can be distinguished from necrosis by the condensation and fragmentation of nuclear material and by the specific cleavage of DNA between nucleosomes. In macrophages and several other cell types exogenous NO delivered from NO donors promoted apoptosis. However, not all cells show the same response to exogenous NO. Thus in human venous endothelial cells low concentrations of an NO donor inhibited apoptosis while higher concentrations promoted apoptosis. In bovine adrenal vascular endothelial cells, apoptosis in response to NO donors was promoted by the presence of a $Ca^{2+}$ ionophore. In primary cultures of hepatocytes NO donors only inhibited apoptosis, and reduced the activation of proteolytic enzymes called caspases which play an important role in the apoptotic process. NO raises cyclic GMP in cells by activating guanylate cyclase. The proapoptotic effects of NO do not seem to involve cyclic GMP but may in some instances be mediated by damage to the DNA and accumulation of p53: antiapoptotic effects of NO can involve cyclic GMP.

Necrosis, on the other hand, can be classified as a form of cell death quite different from apoptosis. Cell necrosis appears to be an unregulated, passive process that is triggered by nonphysiological stimuli, including chemotherapeutic agents. Necrosis does not require energy or the synthesis of proteins and nucleic acids. Morphologically, there are early mitochondrial swelling and failure, dysfunction of the plasma membrane with loss of homeostasis, cell swelling, and rupture. This reaction usually elicits an inflammatory response followed by macrophage phagocytosis. Apoptosis is biologically initiated by the ligation of specific receptors of the tumor necrosis receptor (TNF-R) family. These receptors include CD95/Fas/Apo-1, TNFR1, and the receptor for TRAIL. Ligand binding of the trimerized receptor at the cell surface recruits intracellular adaptor molecules like FADD and TRADD in order to form the death-inducing signaling complex (DISC). Autoactivation of caspase-8 is thought to follow the interaction with the DISC, and cleaves cytosolic Bid to generate a p15 fragment. This fragment translocates to mitochondria and induces the cytochrome c release, which leads to the activation of downstream caspases. The main mitochondrial feature of apoptosis is the permeabilization of the mitichondrial membrane. Mitochondrial dysfunction, or permeability transition pore (PTP), can be caused by several second messengers (calcium, ceramid derivatives, and reactive oxygen species) and pro-apoptotic proteins (Bax, Bak, Bid, and caspases). This allows the escape of cytochrome c. When released from mitochondria, cytochrome c induces oligmerization of Apaf-1, which recruits and activates procaspase-9 in the presence of ATP in a complex called the apoptosome. Caspase-9 activates downstream caspases, including procaspase-3 that are responsible for the cytological changes characteristic of apoptosis. Active caspase-3 preferentially cleaves the inhibitor of caspase-activated DNase (ICAD), and allows the translocation of the activated CAD into the nucleus, resulting in DNA degradation. Therefore, the main biochemical feature of the apoptotic process is the activation of a set of caspase family proteases, and the release of mitochondrial cytochrome c to cytosol.

Overview of the Invention

Figure 2:
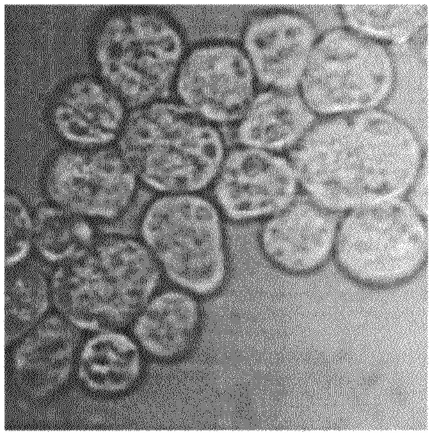
FIG. 2 shows the *Dictyostelium* (strain Ax4) with ingested glycoconjugate-coated *B. cereus* spores (GCSs).
Figure 3:
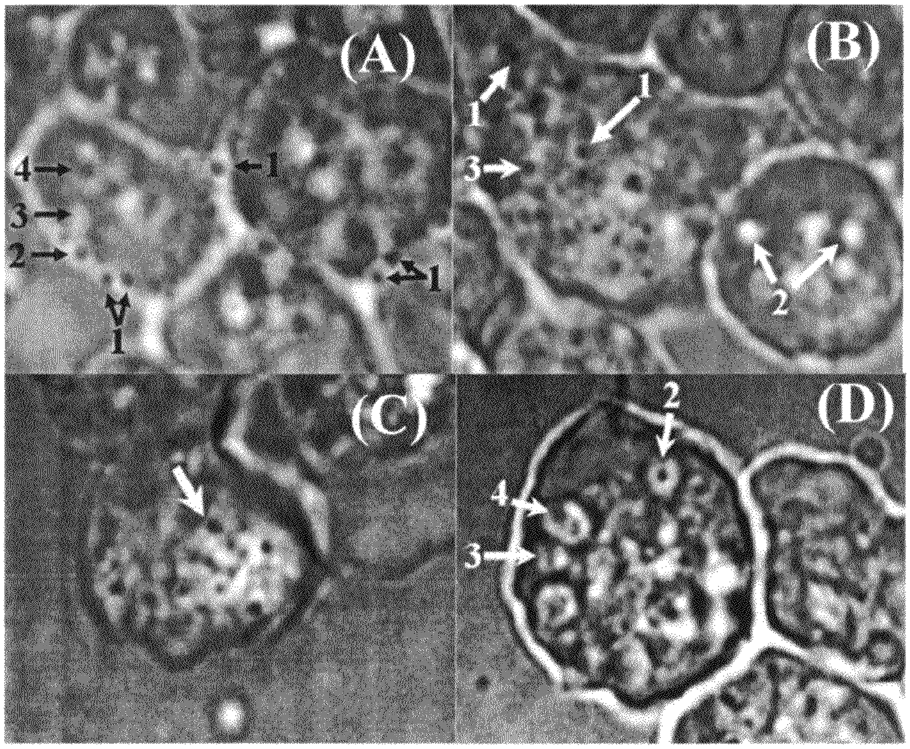
FIG. 3 shows phagocytosis of GCSs by the *Dictyostelium* (strain Ax4) of FIG. 2. The numerical labeling indicates: 1—GCSs adhere to *Dictyostelium*; 2—cytoplasmic vacuoles, called phagosomes, containing GCSs are formed (shown as black dots); 3—lysosomes fuse with the phagosome membrane; 4—a phagolysosome is formed.
Figure 4:
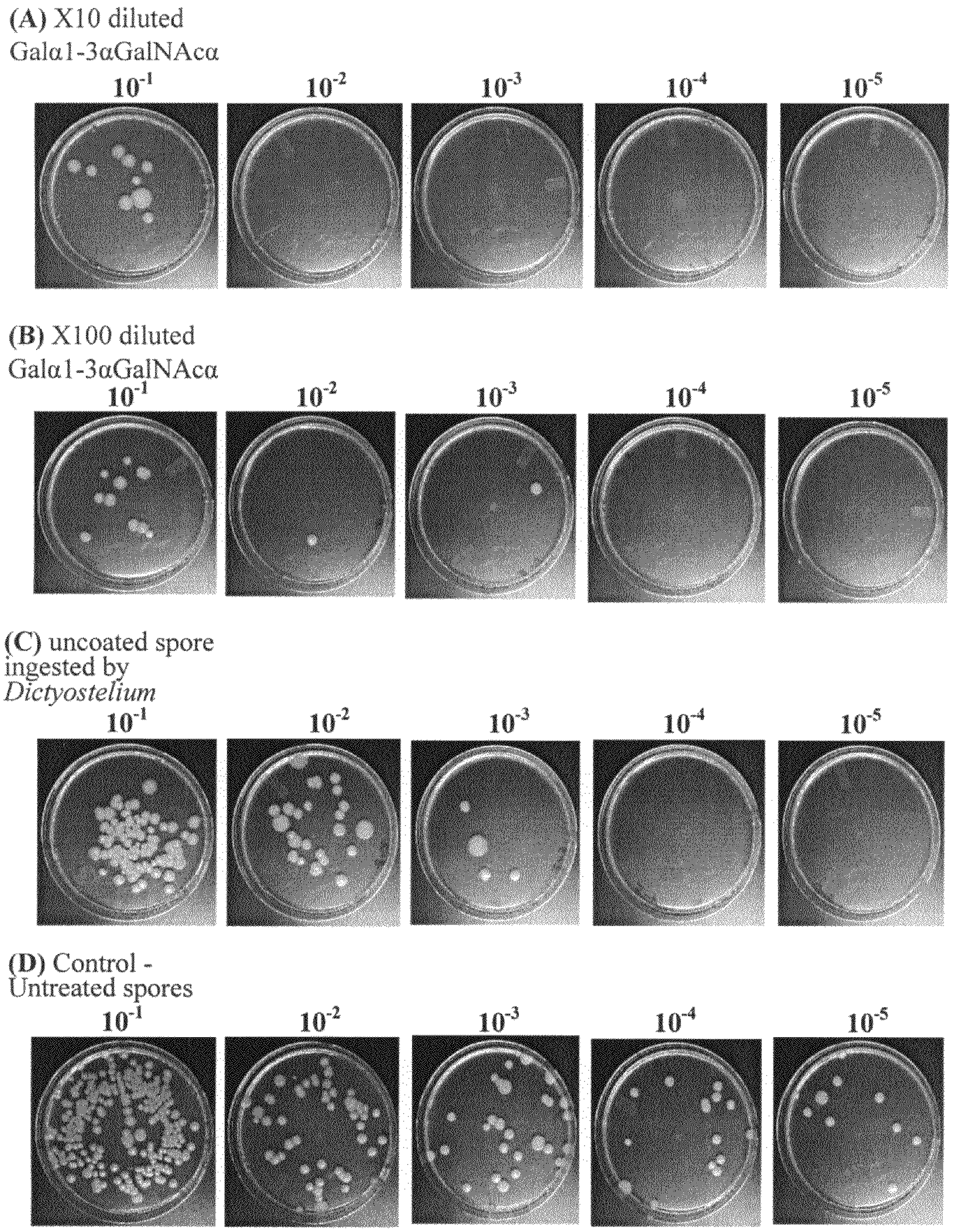
FIG. 4A shows colony forming counts from the serially diluted supernatant extracted from the *Dictyostelium* having ingested the spores coated with 10× diluted Galβ1-3GalNAcα-PAA-flu glycoconjugate.
FIG. 4B shows colony forming counts from the serially diluted supernatant extracted from the *Dictyostelium* having ingested the spores coated with 100× diluted Galβ1-3GalNAcα-PAA-flu glycoconjugate.
FIG. 4C shows colony forming counts from the serially diluted supernatant extracted from the *Dictyostelium* having ingested the uncoated spores.
FIG. 4D shows colony forming counts from the serially diluted supernatant extracted from the control consisting of untreated spores (i.e., untreated by *Dictyostelium*).
Figure 5:
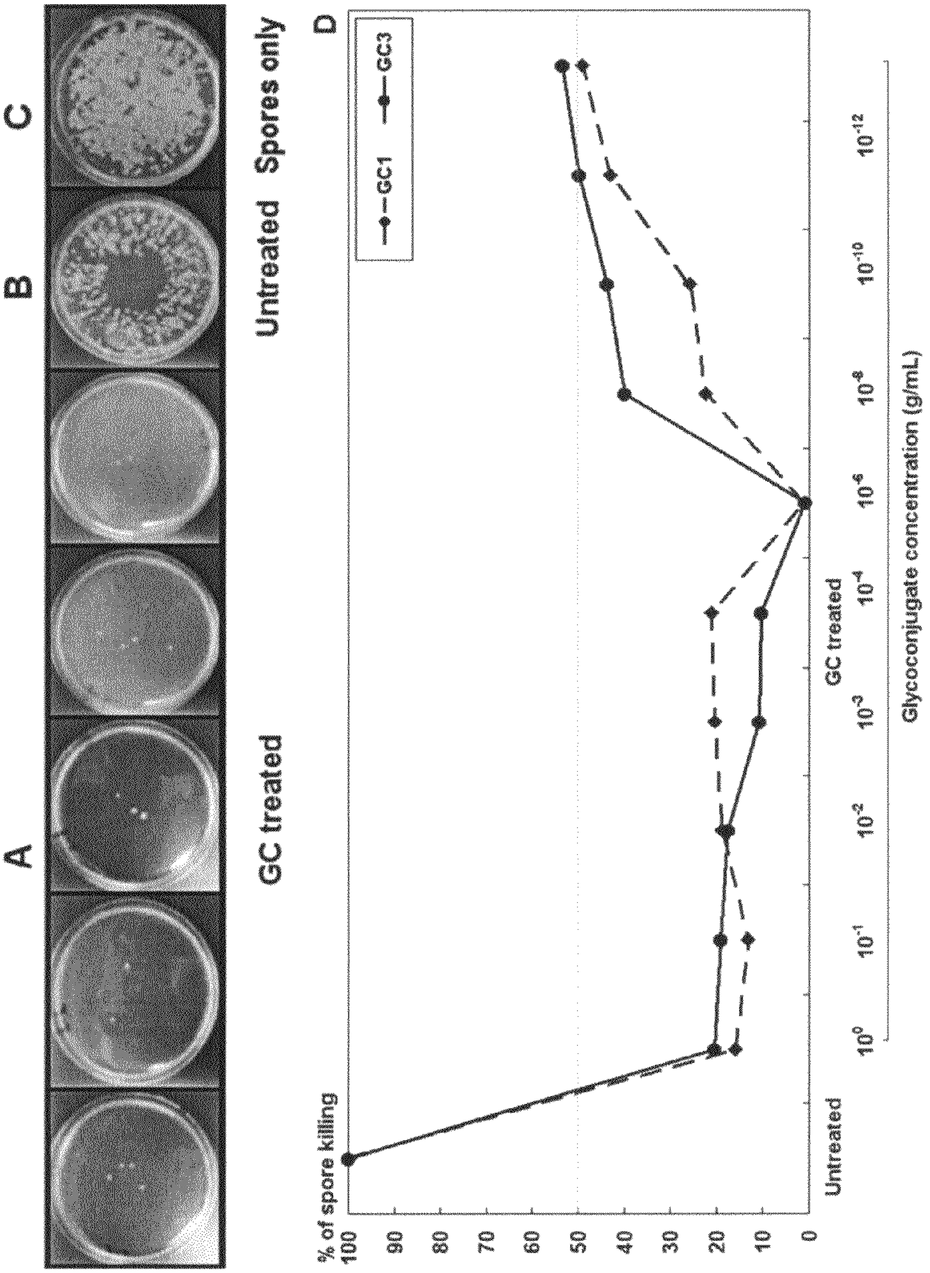
FIG. 5 shows glycoconjugates (GC) facilitate spore destruction by murine macrophages. *B. cereus* spores were treated for 1 hr either with Galα1-3 GalNAcα-PAA-flu (GC1) and GalNAcα1-3 GalNAcβ-PAA-flu (GC3) at studied concentrations and then added to macrophage cultures (A). The same number of untreated spores was added to other macrophage cultures (B) or to culture medium with the absence of macrophages (C). Cultures were then plated for bacterial growth (CFU), $p<0.01$.
Figure 6:
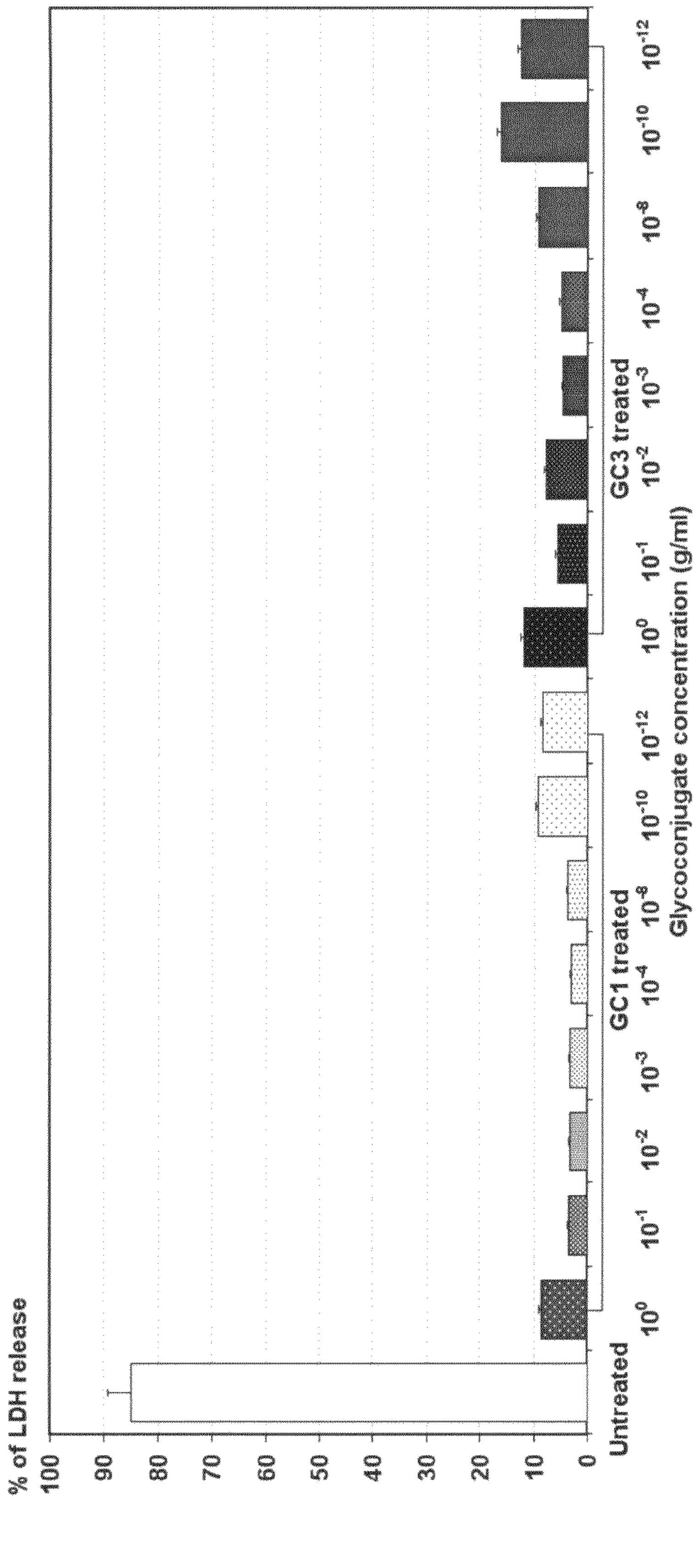
FIG. 6 shows glycoconjugates protected murine macrophages from spore-induced damage. *B. cereus* spores were treated for 1 hr with the glycoconjugates and then added, as described in FIG. 5, to macrophage cultures. After 24 hr, macrophage LDH was assayed in macrophages exposed to untreated spores or to treated spores. These results are representative of duplicate experiments.
Figure 12:
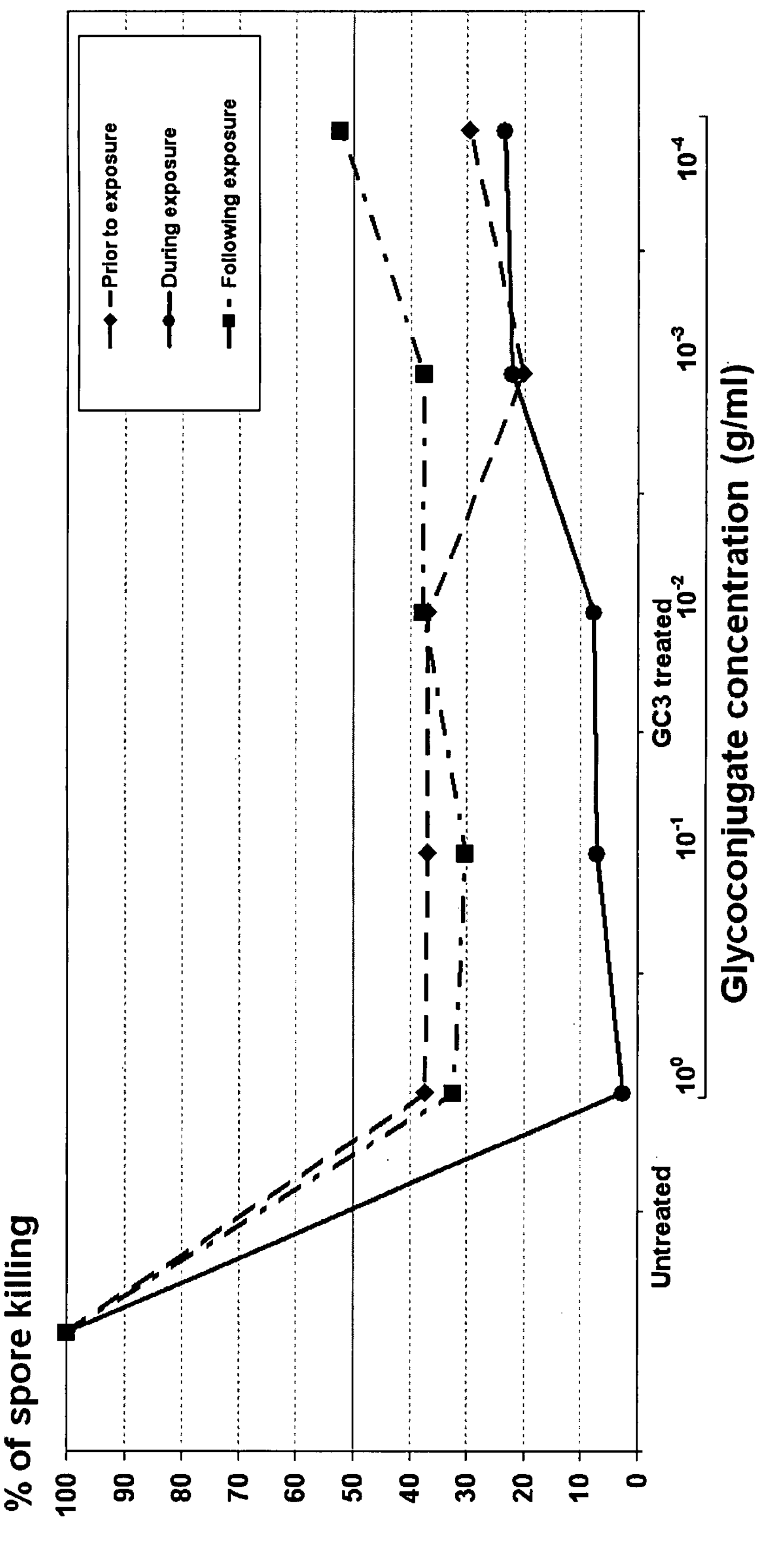
FIG. 12 shows glycoconjugates facilitate spore destruction using human macrophages isolated from peripheral blood mononuclear cells. Three conditions were applied prior to exposure (macrophages were exposed to GCs within 9 hrs, following an infection by spores ($2.4\times10^6$/culture) within 24 hrs); during exposure (macrophages were exposed to GCs coated spores within 24-29 hrs); and following exposure (macrophages were exposed to spores within 9 hrs. GCs were subsequently introduced within 24 hrs). Glycoconjugates concentrations were $10^0$-$10^{-4}$ g/ml. Cultures were then plated for bacterial growth (CFU), $p<0.01$. These results are expressed as mean percent bacterial killing of untreated spores and spores treated with glycoconjugate GC1 or GC3. $LC_{50}$ can be identified for GC#3 for following exposure condition. These results are representative of duplicate experiments.
Figure 13:
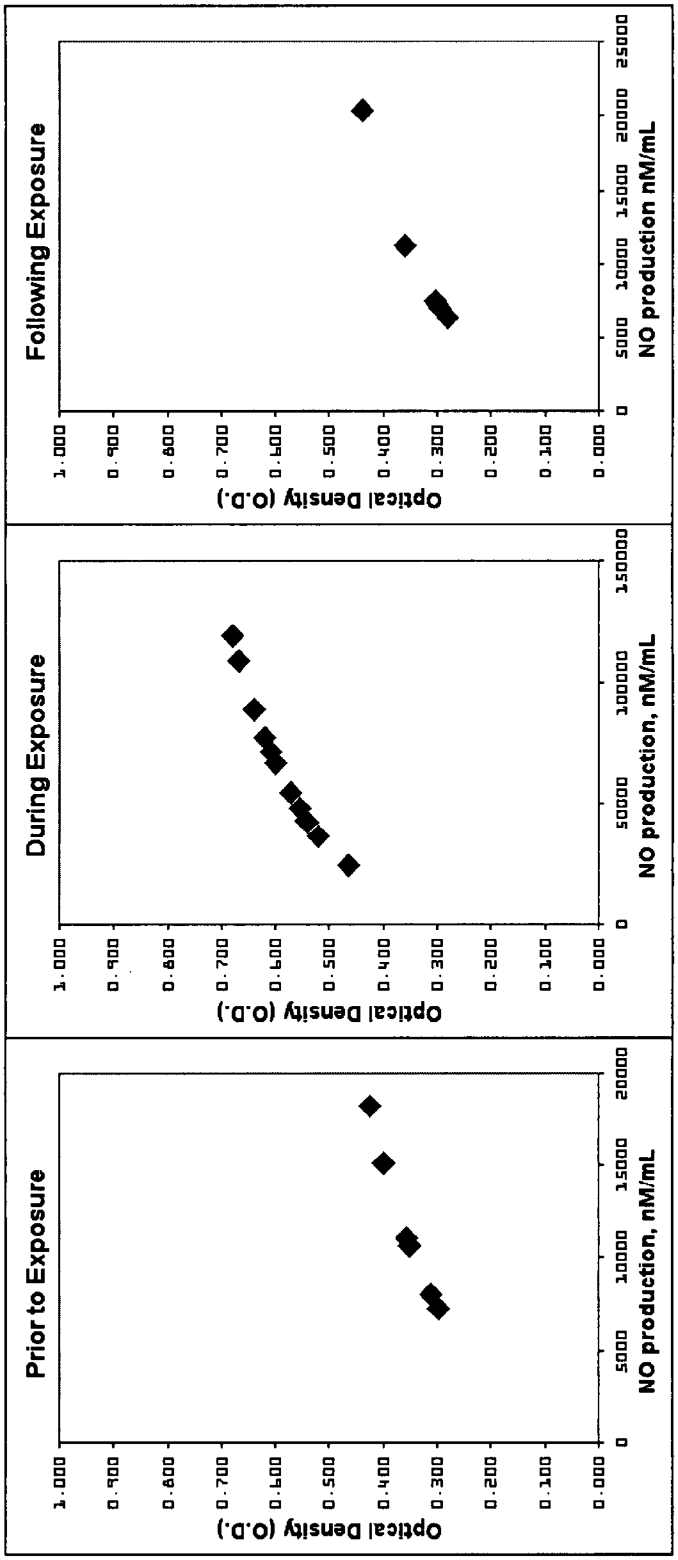
FIG. 13 shows glycoconjugates stimulate human macrophage nitric oxide (NO) production. Macrophage cultures were exposed to untreated spores, as well as to spores GC3-treated with concentration ($10^0$-$10^{-4}$ g/ml). After 24 hrs, macrophage NO production was measured by the Griess assay. Results are representative of duplicate experiments.

The description will be made as to the embodiments of the present invention in conjunction with the accompanying FIGS. 1-14. FIGS. 1-3 demonstrate the stimulatory effects of glycoconjugates on phagocytosis of spores including their uptake (FIG. 1- 3) and digestion (FIG. 3). Phagocytes are more prone to adhere to glycoconjugate-coated spores (FIG. 1-3). Glycoconjugates activate either murine (FIG. 7-9) or human macrophages (FIG. 7-9) and promote uptake (FIG. 1-3,10) and killing of Bacillus cereus spores (FIG. 4-5, 12) during phagocytosis. This results in a higher phagocytosis and destruction (or annihilation) of spores (FIG. 4-5, 12) that prevent germination of spores into bacteria and subsequent production of capsule, proteases, and toxins. Glycoconjugates prevent cytotoxic effects induced either by spores and/or germinated bacteria, capsule, or toxins (FIG. 6). In addition, glycoconjugates facilitate macrophage viability (FIG. 7) and their activation (FIG. 8) upon exposure and spore uptake (FIG. 10). The antimicrobial effect of glycoconjugates against spores is due to the production of a cytocydal agent known as nitric oxide (NO) released either by murine (FIG. 9) or human phagocytic cells (FIG. 13). In return, activation and digestion of glycoconjugate coated spores (FIG. 1-3, 10) cause the release of cytokines (FIG. 11, 14) that activates other immune cells. In accordance with the purposes of this invention, as embodied and broadly described herein, this invention, in one aspect, relates to a method of enhancing phagocytosis of bacterial spores. In particular, the invention relates to a method of enhancing destruction and killing of bacterial spores via phagocytosis. Phagocytosis is a process that includes digestion and destruction of invading microbes and foreign particles [5, 17]. In the process of phagocytosis, a phagocytic cell must find, ingest, destroy and digest the microorganisms [5]. A fundamental requirement for many pathogenic bacteria is to escape phagocytosis. To overcome the resistance, the host's nonspecific defense mechanisms can make microbes more susceptible to phagocytosis [5-9]. If microbes are first coated with antibodies, or with proteins of the complement system, the microbes become more susceptible to binding to phagocytes [5-9]. The present invention provides methods for enhancing the ability of a phagocyte to bind, ingest, destroy and kill bacterial spores by using a glycoconjugate that is capable of modifying bacterial spores surface and make them more susceptible to phagocytosis. The discovery will have an important impact on treatment of bacterial spores that are resistant to killing by the phagocytes that have ingested the bacterial spores, as well as on preparedness against bioterrorism attack, medical response and public health management, rapid disease diagnosis and treatment strategies.

Phagocytosis and Phagocytes

Phagocytosis is a process by which living cells (phagocytes) ingest or engulf other cells or particles. The phagocytic cell may be a free-living one-celled organism, such as an amoeba, or one of the body cells, such as a macrophage or a neutrophil leukocyte (white blood cell), in one of the higher animals.

Phagocytosis starts with the neutrophil or macrophage flowing around the pathogen and engulfing it so that it becomes enclosed in a phagosome (phagocytic vesicle). This is only the first step because it remains a more challenging task of destroying the microorganisms. Some pathogens have special, effective mechanisms for frustrating this destruction step.

The phagosome moves deeper into the cell and fuses with a lysosome, forming a phagolysosome. Lysosomes are derived from the Golgi apparatus, much like secretion vesicles, but their contents are for destroying microorganisms. They contain hydrogen peroxide, active oxygen species (free radicals), peroxidase, lysozyme and hydrolytic enzymes. This is known as the oxidative burst, and leads to digestion of the phagolysosome contents.

Important factors that help destroy microorganisms within a phagolysosome include hydrogen ion transport, oxygen radicals, nitric oxide, anti-microbial proteins, anti-microbial peptides and binding proteins. The significance of each factor is described as follows:

Hydrogen ion transport: Transporters for hydrogen ions acidify the phagolysosome, which kills various microorganisms.

Oxygen radicals: A complex of proteins called NADPH oxidase in the membrane of a phagolysosome generates oxygen radicals in the phagosome. These highly reactive molecules react with proteins, lipids and other biological molecules.

Nitric oxide: Nitric oxide synthase synthesizes nitric oxide, a reactive molecule that damages various biological molecules. However, nitric oxide is also an important regulatory molecule elsewhere.

Anti-microbial proteins: Important are lysozyme, an enzyme that attacks the cell walls of certain (gram positive) bacteria, and special proteases which break down protein when in an acid environment.

Anti-microbial peptides: Defensins and certain other peptides attack bacterial cell membranes.

Binding proteins: Lactoferrin binds iron ions, which are necessary for growth of bacteria. Another protein binds vitamin B12.

Identification of pathogen is important for phagocytosis to occur. Neutrophils and macrophages have some ability on their own to recognize microorganisms and begin phagocytosis. This is because such organisms have molecules much different than those found in a human.

The speed of phagocytosis can be increased markedly by bringing into actions two attachment devices present on the surface of phagocytic cells: Fc receptor and complement receptor. Fc receptor binds the Fc portion of antibody molecules, chiefly IgG. The IgG will have attached the organism via its Fab site. The component of complement (C3) also binds to organisms and then attach to the complement receptor leading to greater internalization by phagocytic cells by opsonization. Therefore, phagocytosis is far more effective if microorganisms are labeled by special molecules that bind to their surface. Any molecule that binds to a microorganism and thereby speeds phagocytosis is called an opsonin.

In one embodiment, the method of destructing and killing a bacterial spore according to the invention is applied to treat a bacterial spore present in a body of a human or a non-human animal having been infected by the spore, the method including subjecting the bacterial spore to an effective amount of a glycoconjugate to form glycoconjugate-coated spores, thereby increasing phagocytosis of the glycoconjugate-coated spore by a phagocyte as compared to that of uncoated spores. Preferably, the method is applied to treat a human or a non-human animal at an early stage of infection by the spore. More preferably, the method is applied to treat the spore that is still present in an extracellular space or in tissue fluid in the body of the human or the non-human animal. When the method is applied to treat the human or non-human animal infected by a spore, a phagocyte used for the phagocytosis is selected from the group consisting of monocyte, macrophage and neutrophil.

The present invention also has applicability in the removal of environmental contaminations by bacterial spores, including anthrax spores. In one embodiment, the invention provides a method of destructing and killing a spore produced by a bacterium, the method including the steps of treating the spore with an effective amount of a glycoconjugate to form a glycoconjugate-coated spore and providing a phagocyte to ingest the glycoconjugate-coated spore, thereby destructing and killing the spore as a result of phagocytosis. The method may further including increasing adherence of the glycoconjugate-coated spores to the phagocyte, whereby increasing the ingestion of the glycoconjugate-coated spores and resulting in increased formation of phagosome compared with that of uncoated spores. Preferably, the method further encompasses the step of increasing phagosome-lysosome fusion in the phagocyte, thereby increasing destruction and killing of the spores by the phagocyte. For environmental decontamination of bacterial spores, any amoebae that can phagocytize foreign particles may be used, which include amoebae *Dictyostelium discoideum.*

Amebas are tiny, one celled organisms in the Protista kingdom that usually can only be seen under a microscope. Amebas vary in size from about 1/100 inch (0.25 millimeter) to 1/10 inch (2.5 millimeters) across. Amebas can live in water, moist soil or in the bodies of animals and human beings. Amebas eat tiny living organisms and particles of dead and decaying matter. They engulf their food by slowly wrapping pseudo pods around a food particle. In this way, the food gets inside the cell and forms a food vacuole. It floats in the protoplasm until the food is digested.

In one embodiment, the method of the invention is used to destruct and kill bacterial spores produced by the bacteria selected from the group consisting of the genus *Clostridium* and the genus *Bacillus*. Preferably, the bacterial spores are produced by *Bacillus cereus* and *Bacillus anthracis.*

Glycoconjugate

According to the invention, any glycoconjugate that can modify a surface of a bacterial spore to increase adherence to a phagocyte may be used. After the surface modification, the glycoconjugate-coated spore (GCS) is ingested by the phagocyte, which then leads to activation of phagocyte, destruction and killing of the spore as a result phagocytosis.

Glycoconjugate is a type of compound consisting of carbohydrate units covalently linked with other types of chemical constituent. A glycoconjugate is a generic term of biomolecules including saccharides and includes glycopeptide, proteoglycan and glycolipid.

Glycoconjugates have been reported to play an important role in pathogen-host interactions and phagocytosis. Human cells bear surface molecules that contain carbohydrates (glycoprotein, and glycolipid) and bacteria bind to these glycoconjugates by the carbohydrate despite very different protein or lipid backbones. *Leishmania*, which are obligatory intracellular parasites in mammalian macrophages, gain entry by receptor-mediated phagocytosis. Their major cell surface glycoconjugate, lipophosphoglycan, has been implicated in playing a role in causing parasites to bind to macrophages [11]. In brain, recognition and phagocytic removal of apoptotic neurons by microglia, the brain macrophages, involve asialoglycoprotein-like lectins (a glycoconjugate) [12]. It has also been shown that a fixed steric arrangement of glycans is necessary for the stimulation of macrophages in vitro [13].

It has been reported that immune adherence facilitates phagocytosis, but the route of intracellular processing depends on the molecular nature of the target and is independent of host complement and antibody. One correlate of bacterial killing via phagocytosis is the fusion of phagosomes with lysosomes [14]. Bacterial surface determines the route of intracellular processing, and addition of lipopolysaccharide, a Toll-like receptor ligand, to microspheres directed their intracellular trafficking, resulting in rapid lysosomal fusion [14]. Rajagopalan et al. has reported that a glycoprotein extract of *Klebsiella pneumoniae*, RU 41.740, directly activated human monocyte-derived macrophages and thus inhibited intracellular multiplication of virulent *Legionella pneumophila* serogroup 1 [14].

Methods for synthesizing oligosaccharide or glycoconjugate are well known in the art [16]. Glycoconjugates consist of oligosaccharides that are glycosidically linked to lipids, to phospholipids, to peptides (O- and N-linkage), and to a combination of all these compounds. Therefore, the synthesis of glycoconjugates consists of the oligosaccharide synthesis, the aglycon synthesis, and then their linkage to yield the target molecule. Commonly, glycoconjugate synthesis follows this convergent strategy, hence the glycosidic linkage between the two moieties is performed at a very late stage. However, in some cases—starting from the oligosaccharide—the aglycon is constructed in a linear strategy because formation of the final glycosidic linkage is not compatible with the completed algycon moiety.

The linking of monosaccharide units through a glycosidic bond is fundamental to the synthesis of oligosaccharides and various glycoconjugates. A method of forming a glycosidic bond has been reported in U.S. Pat. No. 6,960,654. Glycosyltransferases such as β1,4-GalNAc transferase and a β1,3-galactosyltransferase and other enzymes involved in the synthesis of lipooligosaccharides have been disclosed in U.S. Pat. No. 7,078,207.

In one embodiment, glycoconjugates used in the methods of the invention are immunogenic as it can stimulate immune response including phagocytosis. Preferably, glycoconjugates used in the methods of the invention increase adherence of the spore to a phagocyte, thereby resulting in ingestion of the glycoconjugate-coated spore and formation of a phagosome in the phagocyte. More preferably, glycoconjugates used in the methods of the invention can facilitate phagosome-lysosome fusion in a phagocyte. Glycoconjugates used in the invention may be one of a glycan, a glycoprotein, a glycolipid, and any combinations thereof. Preferably, the glycoconjugate is carbohydrate units covalently linked with other types of chemical constituent. More preferably, the glycoconjugate is selected from the group consisting of Galβ1-3GalNAcα-PAA-flu, Galβ1-3GalNAcβ-PAA-flu, Fucα1-3GlcNAcβ-PAA-flu, Fucα1-4GlcNAc-PAA-flu, Fucβ1-3GlcNAcβ-PAA-flu, Galβ1-4GalNAcα-PAA-flu, Galβ1-4Glcβ-PAA-flu, GalNAcα1-3GalNAcβ-PAA-flu, GalNAcα1-3GalNAcα-PAA-flu, GlcNAcβ1-3Galβ-PAA-flu, GlcNAcβ1-4GlcNAcβ-PAA-flu, Galα1-4GlcNAcβ-PAA-flu-PAA-flu, GalNAcβ1-3GalNAcβ-PAA-flu, Glcα1-4Glcβ-PAA-flu, Galα1-2Galβ-PAA-flu, Neu5Acα2-6GalNAcα-PAA-flu, Galα1-6Glcβ-PAA-flu, Galβ1-2Galβ-PAA-flu, Neu5Acα2-3Gal-PAA-flu, Neu5Acα2-6Galβ-PAA-flu, Neu5Gcα2-6GalNAcα-PAA-flu, Neu5Acβ2-6GalNAcα-PAA-flu, Neu5Acα2-3GalNAcα-PAA-flu as a single compound. Still more preferably, the glycoconjugate is a combination thereof.

Pharmaceutical Compositions

To destruct and kill spores present in the body of a human or non-human animal having been infected with the spores, a glycoconjugate capable of increasing phagocytosis of spores is prepared as a pharmaceutical composition suitable for administration by various delivery methods including intraperitoneally, intramuscularly, intradermally, subcutaneously, orally or nasally. By "pharmaceutical composition," it is meant that the composition is formulated into a substance that is to be administered purposefully for treating bacterial spores infection in an individual.

The formulation of the compositions comprising a biologically active glycoconjugate may include suitable pharmaceutical carriers. The glycoconjugate used in the method of the invention are immunogenic without adjuvant, however adjuvants may increase immunoprotective antibody titers or cell mediated immunity response. Such adjuvants could include, but are not limited to, Freunds complete adjuvant, Freunds incomplete adjuvant, aluminium hydroxide, dimethyldioctadecyl-ammonium bromide, Adjuvax (Alpha-Beta Technology), Inject Alum (Pierce), Monophosphoryl Lipid A (Ribi Immunochem Research), MPL+TDM (Ribi Immunochem Research), Titermax (CytRx), toxins, toxoids, glycoproteins, lipids, glycolipids, bacterial cell walls, subunits (bacterial or viral), carbohydrate moieties (mono-, di-, tri- tetra-, oligo- and polysaccharide) various liposome formulations or saponins. Combinations of various adjuvants may be used with the glycoconjugate to prepare the immunogen formulation.

Exact formulation of the compositions will depend on the particular glycoconjugate, the species to be administered and the route of administration.

Such compositions are useful for treating any human or non-human animal having been infected by bacterial spores, such as bovine, ovine, caprine, equine, leporine, porcine, canine, feline and avian species. Both domestic and wild animals may be treated. Humans may also be treated with glycoconjugate compositions.

The route of administration may be any convenient route, and may vary depending on the bacterial spores, the animal to be treated, and other factors. Parenteral administration, such as subcutaneous, intramuscular, or intravenous administration, is preferred. Subcutaneous administration is most preferred. Oral administration may also be used, including oral dosage forms which are enteric coated.

The schedule of administration may vary depending on the endospores and the animal to be treated. Animals may receive a single dose, or may receive a booster dose or doses.

The following examples are not intended to limit the scope of the invention in any manner.

EXAMPLES

Experimental Procedures

1. Bacterial Spores

Bacterial spore suspension of *B. cereus* ATCC 11778 (3.5×106 CFU/0.1 ml) and Tryptic Soy (TS) liquid media were purchased from Raven Biological Laboratories Inc. (Omaha, Nebr.). *Bacillus cereus* (*B. cereus*) is an endemic, soil-dwelling, Gram-positive, rod shaped, beta hemolytic bacteria that causes food borne illness. *B. cereus* bacteria are facultative aerobes, and like other members of the genus *Bacillus* produce spores.

Water W3500, tissue culture grade, was purchased from Sigma-Aldrich (St. Louis, Mo.). Sterile tubes (0.5 ml) and ultra-dishes Petri were obtained from PGF Scientific (Gaithersburg, Md.). Sterile trips were purchased from VWR International (Bridgeport, N.J.). All experiments involving spores handling were carried out under a Biological Safety Cabinet Class IIA/B3 Form a Scientific Inc. (Marjetta, Ohio).

2. *Dictyostelium Discoideum*

The amoebae *Dictyostelium discoideum* (*D. discoideum*) were used to study phagocytosis (FIG. 2) of glycoconjugate-coated spores (GCSs). *D. discoideum* is a soil-living amoeba. Many phases of health and disease depend on the behaviors of individual cells so beautifully displayed in *D. discoideum*. Thus, the organism has been a model system for studying fundamental cellular processes such as cytokinesis, motility, phagocytosis, chemotaxis, signal transduction, etc. *Dictyostelium* amoebae grow as separate, independent cells but interact to form multicellular structures when challenged by adverse conditions such as starvation.

3. Glycoconjugates

Fluoresceinated (PAA-fluor.) glycoconjugates including but not limited to Galβ1-3GalNAcα-PAA-flu, Galβ1-3GalNAcβ-PAA-flu, Fucα1-3GlcNAcβ-PAA-flu, Fucα1-4GlcNAc-PAA-flu, Fucβ1-3GlcNAcβ-PAA-flu, Galβ1-4GalNAcα-PAA-flu, Galβ1-4Glcβ-PAA-flu, GalNAcα1-3GalNAcβ-PAA-flu, GalNAcα1-3GalNAcα-PAA-flu, GlcNAcβ1-3Galβ-PAA-flu, GlcNAcβ1-4GlcNAcβ-PAA-flu, Galα1-4GlcNAcβ-PAA-flu-PAA-flu, GalNAcβ1-3GalNAcβ-PAA-flu, Glcα1-4Glcβ-PAA-flu, Galα1-2Galβ-PAA-flu, Neu5Acα2-6GalNAcα-PAA-flu, Galα1-6Glcβ-PAA-flu, Galβ1-2Galβ-PAA-flu, Neu5Acα2-3Gal-PAA-flu, Neu5Acα2-6Galβ-PAA-flu, Neu5Gcα2-6GalNAcα-PAA-flu, Neu5Acβ2-6GalNAcα, Neu5Acα2-3GalNAcα-PAA-flu were purchased from GlycoTech Inc. (Rockville, Md.) and used to investigate the effects of glycoconjugate on the phagocytosis of spores. Solutions of the glycoconjugate (1.0 g/ml) mentioned above were prepared according to the manufacturer's protocol [16], and then diluted $10^{-1}$-$10^{-12}$ times with PBS/0.2% $NaH_3$ buffer.

4. Glycoconjugates-Coated Spores and Phagocytosis

Ten microliters of Galβ1-3GalNAcα-PAA-flu glycoconjugate, in $10^{-1}$-$10^{-2}$ (×10 and ×100) dilutions, respectively, were added to the *B. cereus* spores suspension (2 μl, $3.5\times10^{6}$ CFU/0.1 ml). The mixtures were incubated at room temperature for one hthe to obtain glycoconjugate-coated spores (GCSs). The GCSs were then fed to *Dictyostelium* cells ($5\times10^{6}$) and the samples were incubated in growth media under the condition of continuous shaking at 20° C. for 20 minutes. Afterwards, the samples were spun by centrifugation for 20 seconds to obtain *Dictyostelium* cell pellets. The *Dictyostelium* cell pellets were washed and re-suspended in growth media. The *Dictyostelium* cells were analyzed and counted using a M 420 1, (Nikon Eclipse E400). Photographs of multicellular development were taken in real time.

5. Destruction of Ingested GCSs

Colony forming units (CFU) counts were employed to study the destruction of ingested GCSs. CFU counts were a direct indication of destruction efficiency. To accomplish this, spore-fed *Dictyostelium* was disrupted with a detergent. The mixture was then sonicated to release entrapped spores for viability studies. Resulting supernatants were serially diluted from $10^{-1}$ to $10^{-5}$ and then plated onto Petri dishes with media. Plates were incubated at 37° C. for 14-16 hours, then CFU were counted

Results

FIG. 1A shows a photograph of *Dictyostelium discoideum* amoebae (strain Ax4). *Dictyostelium* is a haploid eukaryotic organism, being characterized as a "skilled" phagocyte mainly ingesting bacteria [2,3], and an easy manipulative model [4]. FIG. 1B is a photograph of *B. cereus* spores having been coated with Gal β1-3 GalNAcα-PAA-flu glycoconjugate, in which the Gal β1-3 GalNAcα-PAA-flu glycoconjugate-coated spores (i.e., GCSs) are shown as black dots. *B. cereus* spores without being treated with Gal β1-3 GalNAcα-PAA-flu glycoconjugate are shown in FIG. 1C, in which the uncoated *B. cereus* spores are translucent.

FIGS. 2-3 are photographs of multicellular development of *Dictyostelium* cells (strain Ax4) after being fed with GCSs. The photographs were taken in real time. It was shown that the *Dictyostelium* cells, after incubation with GCSs for 20 minutes, were loaded with GCSs (FIG. 2)—a phenomenon of phagocytosis. It was also shown that the *Dictyostelium* cells form multicellular structures after being challenged by the adverse condition.

The results have shown that the glycoconjugate influenced adherence, ingestion, and phagocytosis of GCSs. FIG. 3A shows the GCSs adhered to the surface of *Dictyostelium* cells 1; the GCSs were phagocytized and form cytoplasmic vacuoles 2, or called phagosomes 2 within the *Dictyostelium* cells; phagosome-lysosome fusion 3; and phagolysosome 4 formed. A phagolysosome 4 is an intracellular vesicle formed by fusion of a lysosome with a phagosome. Approximately 10-20 GCSs were ingested by one *Dictyostelium* cell (FIG. 3B), based on a direct microscopic count.

Typically, phagocytic cells have several mechanisms for digesting and destroying ingested microbes. These include lysosomes and other metabolic by-products such as hydrogen peroxide, nitric acid, superoxide ions, and hypochlorite ions. FIG. 3B shows that the GCSs were digested and destroyed by lysosomes found in the cytoplasm of *Dictyostelium*, as indicated by phagosome-lysosome fusion 3 (FIGS. 3A and 3D) and formation of a phagolysosome 4 (FIG. 3D).

Direct microscopic counts do not allow differentiation between live and lifeless spores after being ingested by *Dictyostelium* cells. Therefore, CFU counts were employed to study destruction of ingested GCSs. The results have shown that the glycoconjugate treatment facilitated phagocytosis and the destruction of spores viability in a dose-dependent manner (FIG. 4A-4D).

In summary, the present invention, among other things, provides a method of enhancing phagocytosis of bacterial spores. The method employs glycoconjugate to facilitate adherence, ingestion, destruction and killing of bacterial spores by phagocytes. The present invention has important implications for treatment of spores resistant to phagocytosis as well as for preparedness against bioterrorism attack and public health management.

Murine Macrophages

1. Bacterial Spores

*B. cereus* ATCC 11778 was purchased from Raven Biological Laboratories Inc. (Omaha, Nebr.).

2. Glycoconjugates

Fluoresceinated disaccharide Galα1-3 GalNAcα-PAA-flu (GC1) and GalNAcα1-3 GalNAcβ-PAA-flu (GC3) (GlycoTech, Inc., Rockville, Md.) glycoconjugates were used.

3. Experimental animals

C57BL/6 mice were purchased from Harlan Sprague Dawley, Inc. (Indianapolis, Ind.) and maintained in an AALAC-approved vivarium at the University of Arkansas for Medical Sciences (Little Rock, Ark.). C57BL/6 mice, 6 to 8 weeks old, were injected intraperitoneally with 1 ml of 3% thioglycollate broth (Sigma Chemical Co., St. Louis, Mo.). Four days after injection, mice were euthanized and peritoneal exudate cells were collected by lavage with 5 ml RPMI 1640. Macrophages were plated in 6-well plates at $2\times10^6$/culture in RPMI 1640 containing 10% fetal calf serum, 50 nM 2-mercaptoethanol, 100 U/ml penicillin, and 100 μg/mL streptomycin. After 1 hr of incubation at 37° C. (95% air, 5% $CO_2$), nonadherent cells were removed by washing using RPMI 1640 containing 10% fetal calf serum, 50 nM 2-mercaptoethanol, 100 U/ml penicillin, and 100 μg/mL streptomycin.

4. Spore Inhibition.

To evaluate intracellular spore destruction by macrophages, 0.5 μl of *B. cereus* spores ($2.4\times10^6$ CFU/0.1 ml) were treated with 5 μl serially diluted glycoconjugates ($10^0$-$10^{-12}$) and incubated for 1 hr at room temperature as previously described by the inventor [19, 20]. Untreated spores were used as a control ($2.4\times10^6$ CFU/0.1 ml).

5. Macrophage Exposure to Glycoconjugate-Treated or Untreated Spores

Macrophage cultures ($2\times10^6$/culture) were infected with glycoconjugate-treated or untreated spores ($2.4\times10^6$ CFU) at a ratio of 1.2 spores/macrophage and incubated for about 24 hr. Macrophages were then lysed with 200 μl 10% Triton-X100 and 800 μl of tissue culture water (TCW) to release spores for viability studies (FIG. 5). The resulting pellets were washed three times with 1 ml of sterile, distilled water and centrifuged using an accuSpin Micro centrifuge R (Walham, Mass.) for 10 min at 5,000 rpm. Pellets were serially diluted ($10^{-1}$-$10^{-6}$) and 10 μl of each dilution was plated onto trypticase soy agar petri dishes. Plates were incubated overnight at 37° C. and resulting colony-forming units (CFU) were counted (FIG. 5).

6. Macrophage Studies

Figure 7:
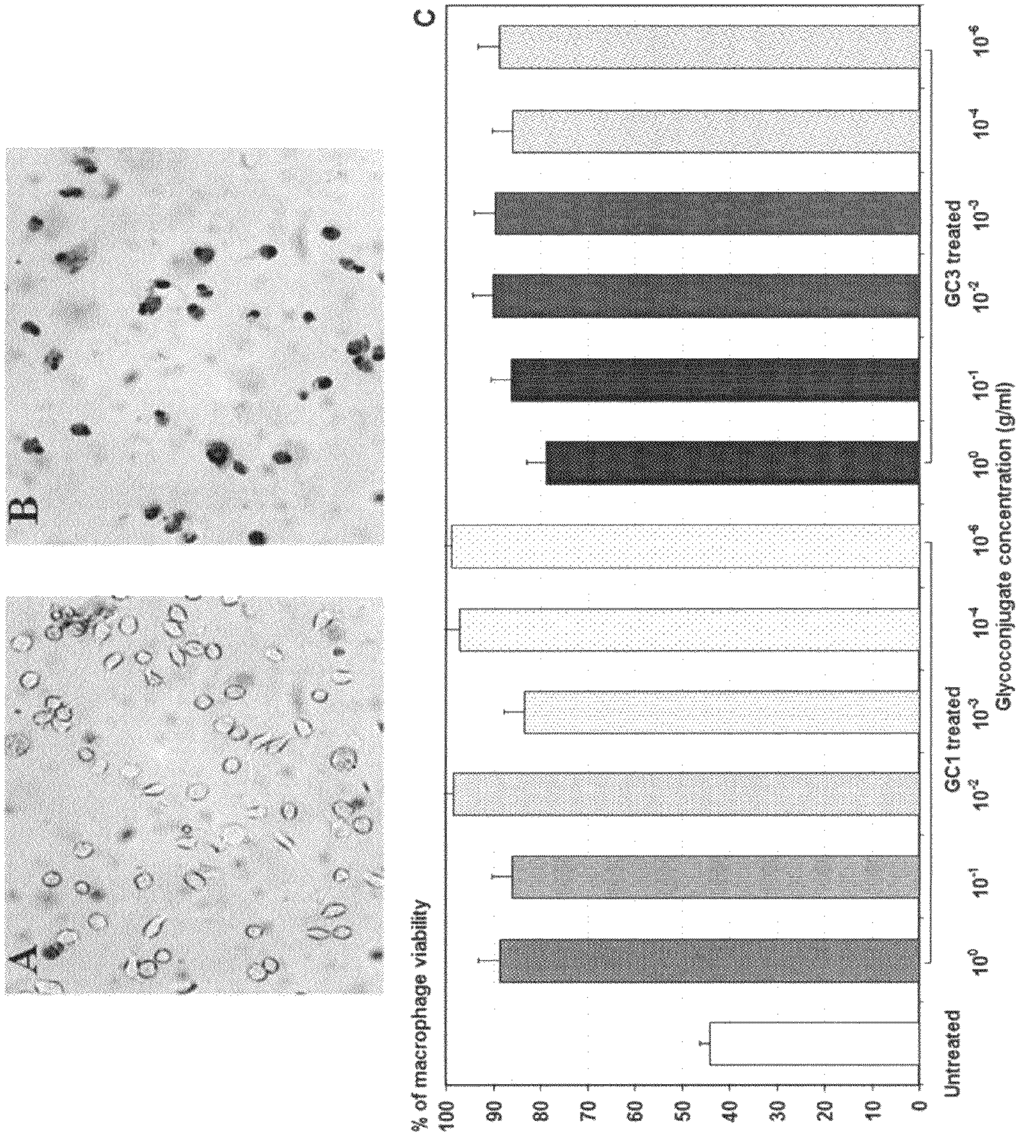
FIG. 7 shows glycoconjugates protected murine macrophage viability after exposure to *Bacillus* spores. Macrophages were exposed to treated (A) or untreated spores (B) and stained for viability with trypan blue 24 hr later. Live macrophages are transparent (A), dead macrophages are stained black/gray (B). The viability for macrophages exposed to untreated and treated spores are shown (C). These results are representative of triplicate experiments.
Figure 8:
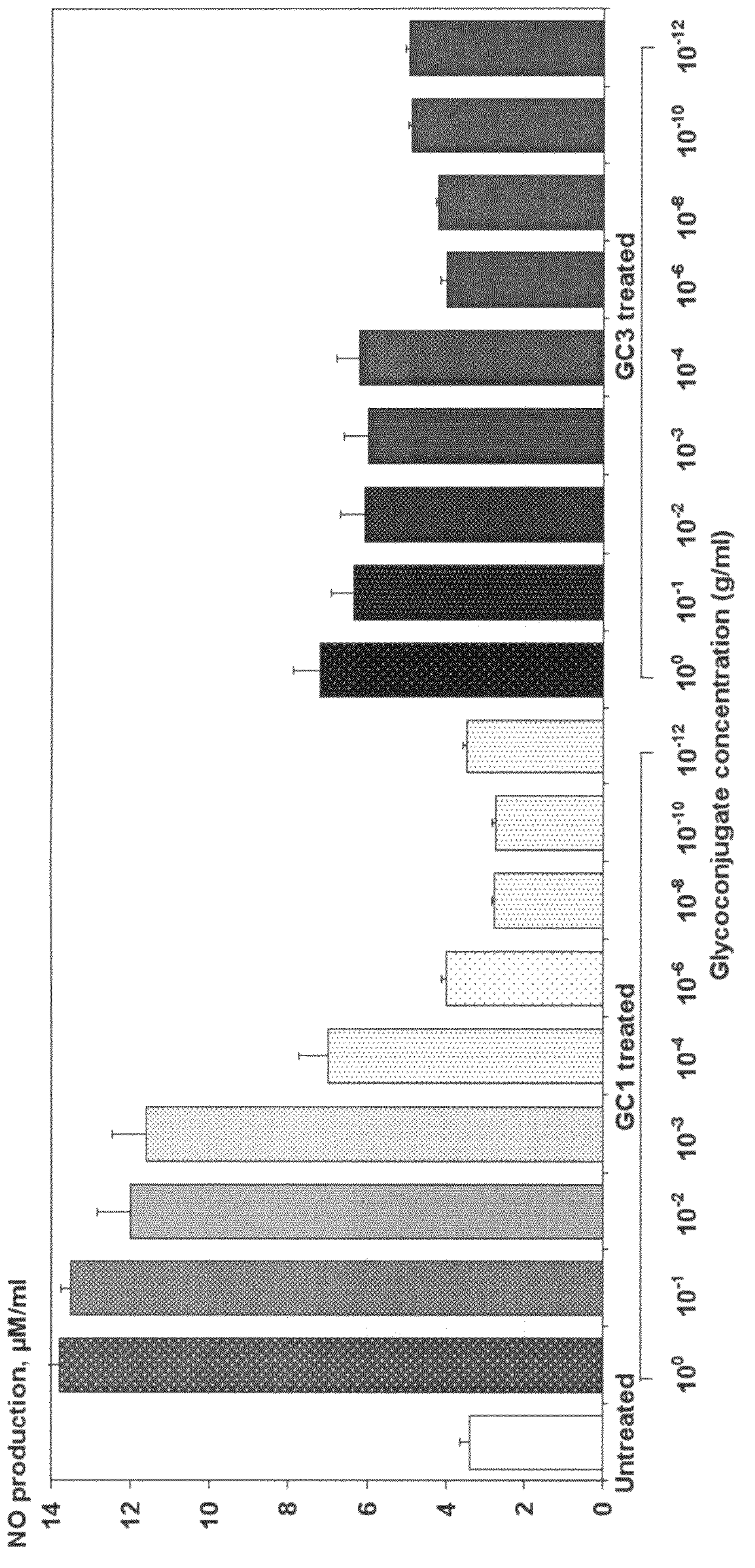
FIG. 8 shows glycoconjugates stimulated murine macrophage nitric oxide (NO) production. Macrophage cultures were exposed to untreated and treated spores. After 24 hr, macrophage NO production was measured by the Griess assay. These results are representative of triplicate experiments
Figure 9:
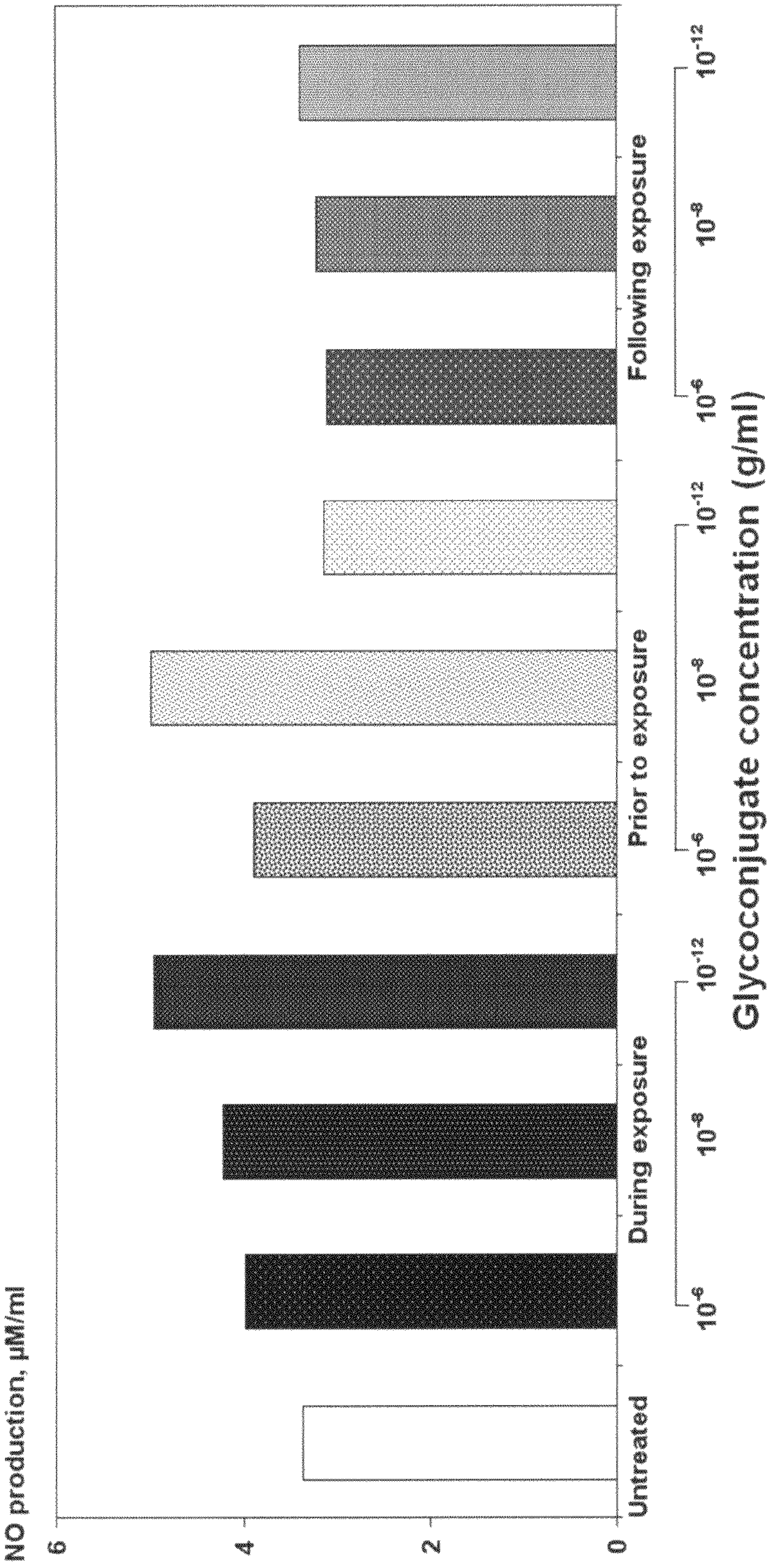
FIG. 9 shows glycoconjugates stimulated murine macrophage nitric oxide (NO) production prior to, during and following exposure. Macrophage cultures were exposed to untreated and treated spores prior to, during and following exposure. Three conditions were applied prior to exposure (macrophages were exposed to GCs within 9 hrs, following an infection by spores ($1.0\times10^6$/culture) within 24 hrs); during exposure (macrophages were exposed to GCs coated spores within 24-29 hrs); and following exposure (macrophages were exposed to spores within 9 hrs. After 24 hr, macrophage NO production was measured by the Griess assay. These results are representative of triplicate experiments.
Figure 10:
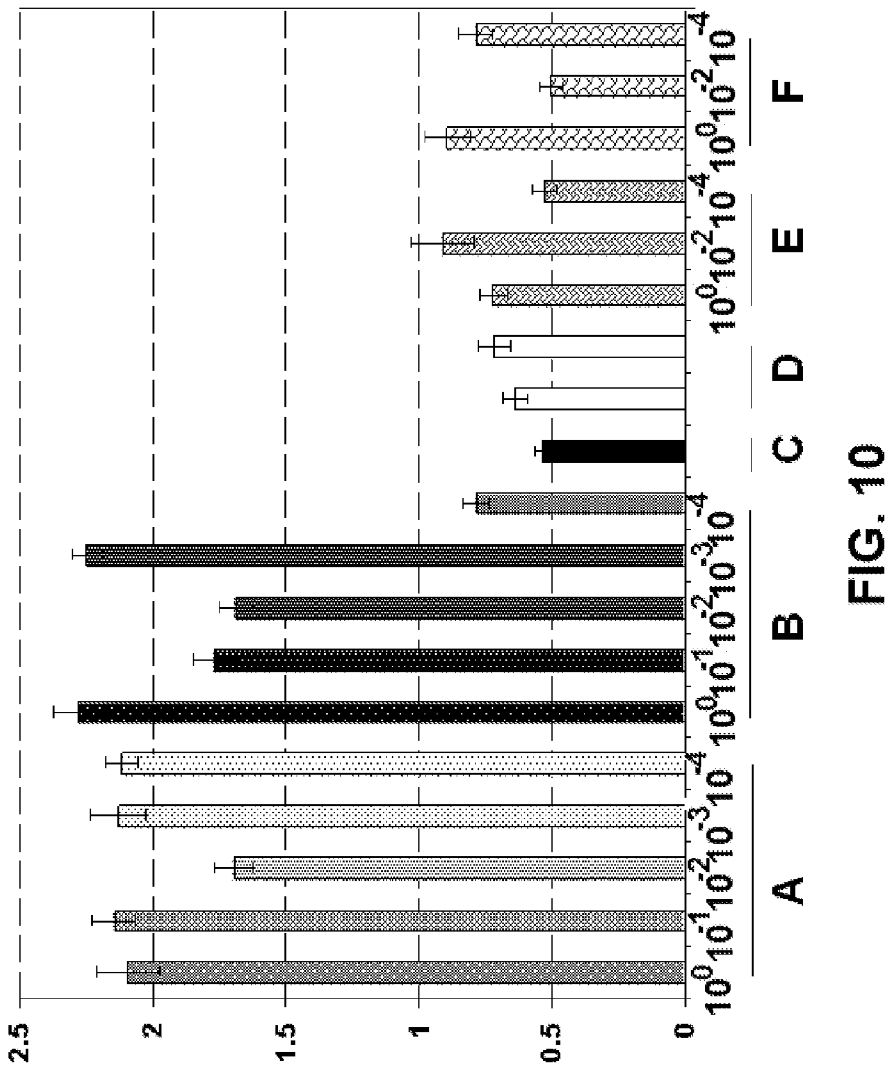
FIG. 10 shows Comet assay based on tail vs. head of GC1 (A) and GC3 treated spores (B), macrophages only (C), macrophages exposure untreated spore (D), macrophages exposed to glycoconjugates only either GC1 (E) or GC3 (F). Diameters of phagocytes exposed to GC1 and GC3-coated (A, B) and uncoated spores and glycoconjugates are shown. GC1 (A) or GC3 (B) treatment stimulates the uptake of coated spores and protect from spore-induced cell death. The diameter of phagocytes increased upon uptaking glycoconjugate-coated spores (A-B) compared to macrophages only (C), spores only (D), and/or GC1 and GC3 glycoconjugate alone (E, F). The higher the stimulatory effects of glycoconjugates are, the more glycoconjugate-coated spores will be ingested by macrophages. The uptake of either uncoated spores (D) or GC1 and GC3 glycoconjugates alone (E, F) do not affect the diameter of phagocytic cells. Dilution of used glycoconjugates ($10^0$, $10^{-1}$, $10^{-2}$, $10^{-3}$, and $10^{-4}$) upon uptake of coated spore (A, B) and glycoconjugates only ($10^0$, $10^{-2}$, $10^{-4}$) (E, F) are shown and compared with macrophages only (C) and spores only (D).

Spore-induced macrophage damage was measured by cell morphology (FIG. 7), trypan blue (FIG. 7), lactate dehydrogenase (LDH) release (FIG. 6), and nitric oxide production (FIG. 8-9). To determine cell viability, the culture supernatants were replaced with 500 μl of 0.4% trypan blue solution and examined microscopically. Percent viability was determined by counting individual live/dead macrophages. Seven determinations were made for each culture well.

Macrophage integrity (FIG. 7) was analyzed using CytoTox 96® kit (Promega, Inc., Madison, Wis.). LDH is a stable cytosolic enzyme released upon cell lysis with conversion of tetrazolium salt (INT) to a red formazan product. The amount of color was proportional to the number of lysed cells (FIG. 7). The absorbance was measured at 490 nm using a Bio-Tek Ex800 plate reader.

For nitric oxide (NO) production, macrophages were plated at $1.0\times10^6$ cells/culture in 6-well flat-bottomed tissue culture plates and incubated with glycoconjugate-treated or untreated spores. Cells were incubated at 37° C. in 5% $CO_2$ for 24 hr. Supernatants (100 μl) were then assayed for NO (FIG. 8). The nitrite ion ($NO_2^-$) concentration, indicative of NO, was determined using $NaNO_2$ as a standard. Briefly, 100 μl of cell culture supernatant was mixed with an equal volume of Griess reagent [0.1% (w/v) N-(1-naphthyl)ethylenediamine dihydrochloride and 1% (w/v) sulfanilamide in 5% (v/v) phosphoric acid] (Cat. 03553-100 ML, Sigma). The samples were incubated at room temperature for 20 min and absorbance was measured at 490 nm using a Bio-Tek Ex800 plate reader. NO production by activated macrophages was studied under three conditions including (FIG. 9): A) prior to exposure (macrophages were exposed to GCs within 9 hrs, following an infection by spores ($2.4\times10^6$/culture) within 24 hrs); B) during exposure (macrophages were exposed to GCs coated (or treated) spores within 24-29 hrs); and following exposure (macrophages were exposed to spores within 9 hrs. GCs were subsequently introduced within 24 hrs). Glycoconjugates concentrations were $10^{-6}$-$10^{-12}$ g/ml.

Possible induction of apoptosis was determined by Comet assay (FIG. 10) using Trevigen (Gaithersburg, Md.) Comet assay kit and analyzed under epifluorescence microscope (FIG. 10). Nuclei with damaged DNA have the appearance of a comet with a bright head and a tail, whereas nuclei with undamaged DNA appear round, with no tail. Ration tail vs. head was measured in order to determine apoptosis (FIG. 10).

Figures 11A, 11B, 11C, 11D:
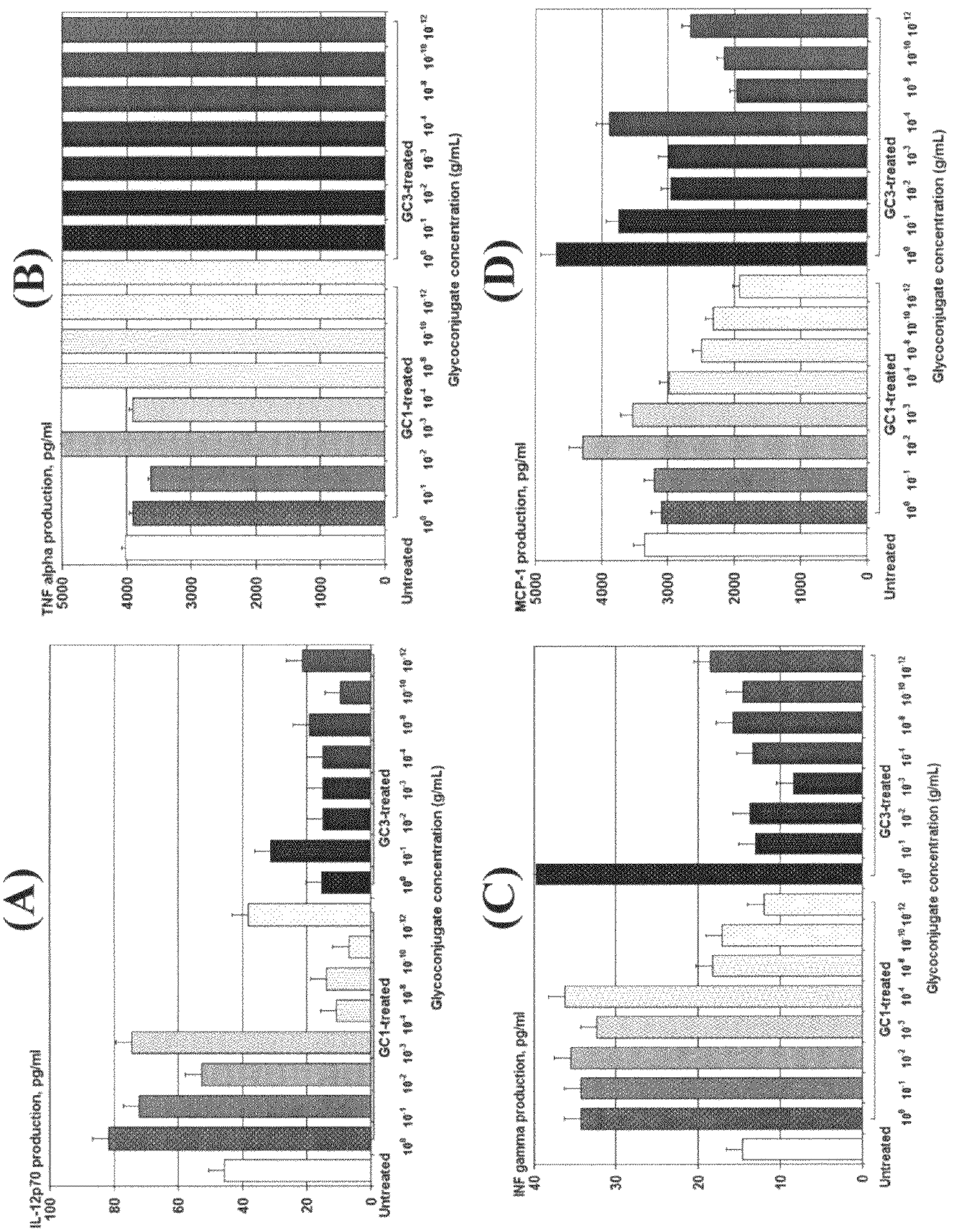
FIG. 11 shows glycoconjugates stimulated cytokines production during phagocytosis. Macrophage cultures were exposed to untreated and GC1 and GC3 treated spores. After 24 hr, macrophage cytokines production was measured using the BD™ Cytometric Bead Array (CBA). IL-12p70 (A); TNF-alpha (B), INF gamma (C); MCP-1 (D); IL-6 (E); IL-10 (F) are shown. Glycoconjugates concentrations $10^0$-$10^{-12}$ were used. These results are representative of duplicate experiments.
Figures 11E, 11F:
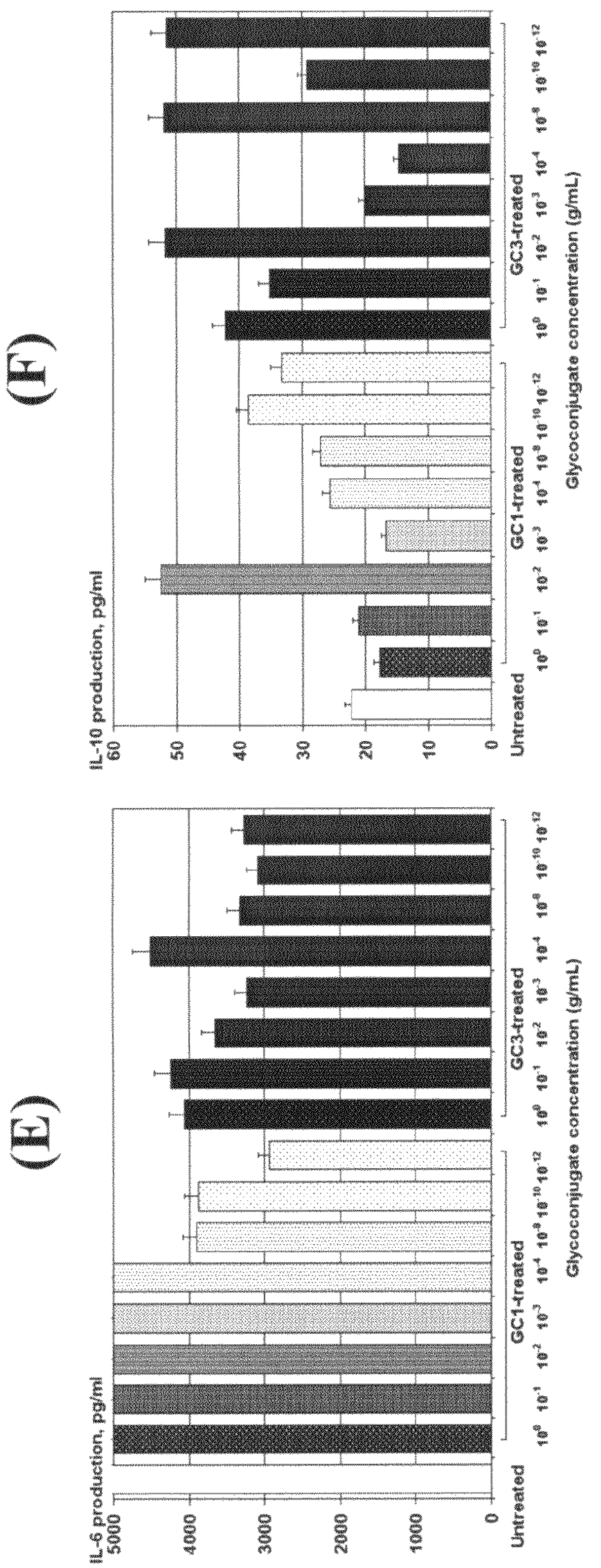

Murine macrophage production of inflammatory cytokines, including IL-6, IL-10, IL-12, tumor necrosis factor (TNF)-α, and monocyte chemoattractant protein (MCP)-1 (FIG. 11) were measured using a cytokine cytometric bead array kit (BD Biosciences, Calif.) (FIG. 11).

7. Statistics

Results were considered statistically significant at p-values <0.01 using AVONA ANOVA. A Tukey test was performed for post-ANOVA.

Results

Following exposure to *Bacillus* spores, they will be rapidly taken up by phagocytes including but not limited to macrophages and/or neutrophil leukocyte. Glycoconjugates were evaluated for the ability to modulate macrophage-mediated destruction of *Bacillus* spores during phagocytosis (FIG. 5). The addition of glycoconjugate Galα1-3 GalNAcα-PAA-flu resulted in almost total destruction of the spores (FIG. 5). As shown in FIG. 5, glycoconjugate Galα1-3GalNAcα-PAA-flu facilitated the destruction of 89.4% ($p<0.01$) of spores, while glycoconjugate GalNAcα1-3GalNAcβ-PAA-flu facilitated the destruction of 86.4% of spores ($p<0.01$) compared to untreated spores. To judge the efficacy of glycoconjugates, these were diluted to $10^{0}$-$10^{-12}$ prior to addition to spores. Results showed that 50% of the spores were killed at a dose of only 1 pg/ml Galα1-3GalNAcα-PAA-flu glycoconjugates or 100 pg/ml GalNAcα1-3GalNAcβ-PAA-flu glycoconjugate (FIG. 5).

The ability of phagocytes to kill the organisms will determine whether the exposure will progress to a possibly serious infection. Exposure of murine macrophages to *B. cereus* spores at a ratio of 1.2 spores/macrophage resulted in macrophage death 24 hr later. This was demonstrated by LDH (FIG. 6) and trypan blue (FIG. 7) assays.

To further characterize the glycoconjugates, their effects on spore-induced damage to macrophages were examined. One day after macrophage exposure to treated or untreated spores, LDH release was determined (FIG. 6). LDH analysis showed that macrophages exposed to untreated spores released 85% of LDH (FIG. 6). Glycoconjugate GalNAcα1-3GalNAcβ-PAA-flu induced 11.9% LHD production, whereas 8.9% LDH was observed with glycoconjugate Galα1-3GalNAcα-PAA-flu ($p<0.01$) (FIG. 6).

As shown in FIG. 7, dilution of the glycoconjugates as much as a million fold did not attenuate the protective effect for macrophages. This was consistent with a dramatic loss of macrophage viability following exposure to untreated *B. cereus* spores (FIG. 7A). In contrast, the glycoconjugates protected the macrophages from spore-induced loss of viability (FIG. 7B, C). The presence of either GalNAcα1-3 GalNAcβ-PAA-flu or Galα1-3 GalNAcα-PAA-flu glycoconjugates induces macrophage viability up to 87% and 97.8%, respectively (FIG. 7C). Viability of macrophages exposed to untreated spores was only 44% (FIG. 7C).

Since macrophage NO production is important in the killing of phagocytized bacteria and a marker of macrophage activation [6, 12, 13], the effects of the glycoconjugates on macrophage NO production were examined (FIG. 8). Macrophages were exposed to spores, but were not otherwise activated. In the absence of glycoconjugates, *B. cereus* spores killed most of the macrophages without inducing more than background NO production (FIG. 8). The presence of either Galα1-3GalNAcα-PAA-flu or GalNAcα1-3GalNAcβ-PAA-flu glycoconjugate induced macrophage NO production ($p<0.0001$). Glycoconjugate Galα1-3GalNAcα-PAA-flu doubled macrophage NO production, while glycoconjugate GalNAcα1-3GalNAcβ-PAA-flu was less stimulatory. In general, NO production decreased with increasing dilution of the glycoconjugates (FIG. 8). NO production was stimulated most likely prior and during exposure of spores (FIG. 9).

The present invention primarily focused on glycoconjugates and their protective role in macrophages exposed to *B. cereus* spores. The presence of glycoconjugates prevented the widespread death of macrophages exposed to the spores (FIG. 7). Moreover, the macrophages were able to efficiently kill the organisms (FIG. 5). The glycoconjugates bound to the spores might also act as opsonins, promoting phagocytosis. Even when highly diluted, glycoconjugates were very effective at protecting the macrophages from cell death (FIG. 7) and promoting killing of the *Bacillus* organisms (FIG. 5).

The results show that glycoconjugates promote activation of macrophages and kill spores (FIG. 5), viability of macrophages (FIG. 7) and lower LDH production (FIG. 6). There is some evidence that glycoconjugates can serve as chemoattractants and/or immunostimulators for macrophages. Indeed, the glycoconjugates increased macrophage production of inducible NO, which is important in the intracellular killing of *B. cereus* spores (FIG. 8). Different glycoconjugates may exhibit different activities and this may be reflected by the differences observed in inducible NO production by macrophages prior to, during, and following exposure to the bacterial spores (FIG. 9). Furthermore, it was shown that a high level of NO can promote apoptosis in some cells, whereas lower NO levels inhibit apoptosis in others. Not all cells may show the same response to exogenous NO (FIG. 8, 9). It was shown than in macrophages and several other cell types exogenous NO delivered from NO donors promotes apoptosis.

Apoptosis, or programmed cell death, is a strictly regulated device that is responsible for the ordered removal of superfluous, aged, or damaged cells Apoptosis or programmed cell death is believed to occur by either necrotic or apoptotic mechanisms. Apoptosis, or programmed cell death morphologically characterize by flowing in cells undergoing apoptosis there is ruffling, blebbing, and condensation of the plasma and nuclear membranes, and subsequently aggregation of the nuclear chromatin; mitochondria and ribosomes retain their gross structure, and at the least, partial function; there is also disruption of the cytoskeletal architecture; the cell shrinks, and then fragments into a cluster of membrane-enclosed "apoptotic bodies" that are rapidly ingested by adjacent macrophages or other neighboring phagocytic cells; apoptotic cells display a characteristic fragmentation pattern of DNA into distinct segments that can be visualized as a ladder of bands by gel electrophoresis.

Uncoated spores rather do not induce death (FIG. 10C). GC1 (FIG. 10A) or GC3 (FIG. 10B) treated spores have pro-apoptotic effects on murine macrophages. Macrophages treated with either GC1 or GG3 do not induce death (FIGS. 10E and 10F) and promote macrophage survival (FIG. 7) and activation (FIGS. 8, 9 and 12). For instance, human venous endothelial cells low concentrations of an NO donor inhibited apoptosis while higher concentrations promoted apoptosis. Apoptosis can be distinguished from necrosis by the condensation and fragmentation of nuclear material and by the specific cleavage of DNA between nucleosomes. NO may raise cyclic GMP in cells by activating guanylate cyclase. Furthermore, NO antiapoptotic effects of NO can involve cyclic GMP. The pro-apoptotic effects of NO may not involve cyclic GMP and may characterize by damage to the DNA and accumulation of p53. Necrosis can be classified as a form of cell death quite different from apoptosis. Cell necrosis appears to be an unregulated, passive process that is triggered by non-physiological stimuli, including chemotherapeutic agents; necrosis does not require energy or the synthesis of proteins and nucleic acids. Necrosis is morphologically characterized by early mitochondrial swelling and failure, dysfunction of the plasma membrane with loss of homeostasis, cell swelling, and rupture. Necrosis usually elicits an inflammatory response followed by macrophage phagocytosis.

Taken together, glycoconjugates stimulate and activate macrophages. Glycoconjugates have a protective influence, sparing macrophages from spore-induced cell death, enhance phagocytosis and destruction spores of agents. Glycoconjugates prevent cell death of macrophages at very low concentrations as shown by LDH release (FIG. 6) and TB assays (FIG. 7). Activated macrophages produce NO (FIG. 8). Increased levels of inducible NO production by macrophages in the presence of glycoconjugates suggested that the glycoconjugates provide an activation signal on the cellular target. NO is antimicrobial, bactericidal agent that kill spores (FIG. 5). NO production is important in killing phagocytized bacteria and a marker of macrophage and/or other immune cells activation. Furthermore, NO is a transducer of the vasodilator message from the endothelium to the vascular smooth muscle. It is also a neurotransmitter in the central and peripheral nervous systems, and participates in non-specific immune responses (for instance production of cytokines).

Apoptosis can elicit secondary immune response. Glycoconjugates stimulate activated phagocytic cells to produce cytokines for instance IL-12p70, TNF-alpha, INF-gamma, MCP-1, IL-10, IL-6 (FIG. 11). Cytokines express a cytokine-inducible NOS isoform and or other isoforms in many cells including macrophages after the stimulation of immunological or inflammatory reactions; this produces large amounts of NO for several days (FIGS. 8 and 9). Analysis has shown that NO was lasting more than 29 hours under prior and during exposure conditions (FIG. 9)

Human Macrophages

1. Bacterial Spores

*B. cereus* ATCC 11778 was purchased from Raven Biological Laboratories Inc. (Omaha, Nebr.).

2. Glycoconjugates

Fluoresceinated disaccharide glycoconjugate GalNAcα1-3 GalNAcβ-PAA-flu (GC3) (GlycoTech, Inc., Rockville, Md.) was used.

3. Isolation of Human Macrophages

Blood samples were obtained from volunteering donors. Blood was drawn on heparin using phlebotomy. Isolation of human mononuclear cells was performed from peripheral blood (PBMC) on 20 ml of Ficoll-Paque Plus (Cat. NC9778355, Fisher) solution by centrifugation within 20 min (22° C., 1500 rpm, accel 6 and no brake). PBMC were isolated from the interface between plasma and erythrocyte/granulocyte pellets into new sterile 50 ml tube. PBMC (macrophages and neutrophils) washed once with basal medium (RPMI 1640 with glutamine containing 10% fetal calf serum, 50 nM 2-mercaptoethanol, 100 U/ml penicillin, and 100 μg/mL streptomycin) by centrifugation in sterile tube within 20 min at 22° C., 1500 rpm, accel 6 and no brake. Obtained PBMC cells were resuspended in 36.0 ml of basal media (RPMI 1640 with glutamine containing 10% fetal calf serum, 50 nM 2-mercaptoethanol, 100 U/ml penicillin, and 100 μg/mL streptomycin) and plated 6-wells plate ($2.25\times10^5$/well). Soon after, 1 ml of basal media (RPMI 1640 with glutamine containing 10% fetal calf serum, 50 nM 2-mercaptoethanol, 100 U/ml penicillin, and 100 μg/mL streptomycin) was added into each well of a 6-wells plate and incubated within 1 hr at 37° C. (95% air, 5% $CO_2$). After 1 hr of incubation at 37° C. (95% air, 5% $CO_2$), nonadherent cells were removed by washing using basal media (RPMI 1640 with glutamine containing 10% fetal calf serum, 50 mM 2-mercaptoethanol, 100 U/ml penicillin, and 100 μg/mL streptomycin).

4. Spore Inhibition.

To evaluate intracellular spore destruction by human macrophages (FIG. 12), 0.5 μl of *B. cereus* spores ($2.4\times10^6$ CFU/0.1 ml) were treated with 5 μl serially diluted glycoconjugates ($10^0$- $10^{-12}$) and incubated for 1 hr at room temperature as previously described by the inventor [19, 20. Untreated spores were used as a control ($2.4\times10^6$ CFU/0.1 ml).

5. Phagocytosis Prior to, During, and Following Exposure of Treated or Untreated Spores Using Human Macrophages Macrophage cultures ($2\times10^6$/culture) were infected with glycoconjugate-treated or untreated spores ($2.4\times10^6$ CFU) and incubated for about 24 hr. Macrophages were then lysed with 200 μl 110% Triton-X100 and 800 μl of tissue culture water (TCW) to release spores for viability studies (FIG. 12). The resulting pellets were washed three times with 1 ml of sterile, distilled water and centrifuged using an accuSpin Micro centrifuge R (Walham, Mass.) for 10 min at 5,000 rpm. Pellets were serially diluted ($10^{-1}$-$10^{-6}$) and 10 μl of each dilution was plated onto trypticase soy agar petri dishes. Plates were incubated overnight at 37° C. and resulting colony-forming units (CFU) were counted (FIG. 10). Spore phagocytosis by human macrophages was studied under three conditions including: A) prior to exposure (macrophages were exposed to GalNAcα1-3 GalNAcβ-PAA-flu (GC3) within 9 hrs, following an infection by spores ($2.4\times10^6$/culture) within 24 hrs); B) during exposure (macrophages were exposed to GC3-treated spores within 24-29 hrs); and following exposure (macrophages were exposed to spores within 9 hrs. GC3 was subsequently introduced within 24 hrs) (FIG. 12). Glycoconjugate concentration was $10^0$-$10^{-4}$ g/ml.

6. Macrophage Studies

Figures 14A, 14B, 14C, 14D:
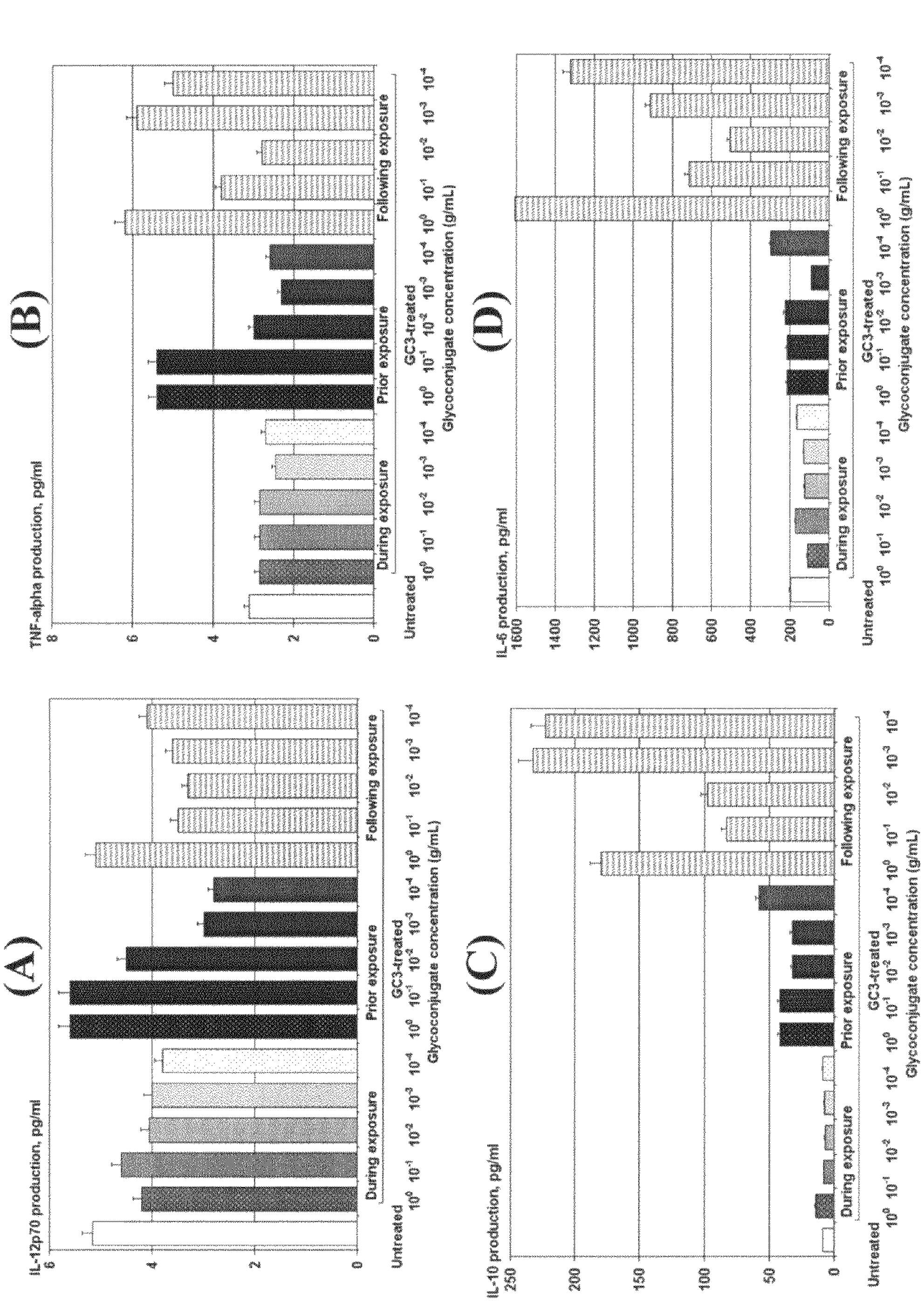
FIG. 14 shows glycoconjugates influence cytokines production by human macrophages during phagocytosis. Three conditions were applied prior to exposure (macrophages were exposed to GCs within 9 hrs, following an infection by spores ($2.4\times10^6$/culture) within 24 hrs); during exposure (macrophages were exposed to GCs coated spores within 24-29 hrs); and following exposure (macrophages were exposed to spores within 9 hrs. GCs were subsequently introduced within 24 hrs). Glycoconjugates concentrations were $10^0$-$10^{-4}$ g/ml. Supernatants were assayed using the BD™ Cytometric Bead Array (CBA). IL-12p70 (A); TNF-alpha (B), IL-10 (C); IL-6 (D); IL-1B (E) are shown. Glycoconjugates concentrations $10^0$-$10^{-12}$ were used. These results are representative of duplicate experiments.
Figure 14E:
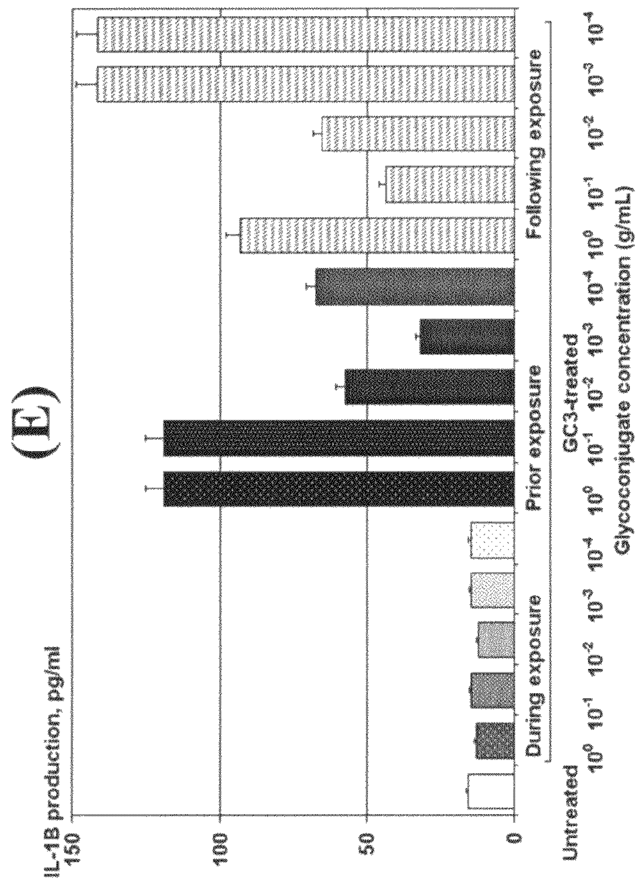

Macrophage activation prior to, during, and following exposure of treated or untreated spores was measured by nitric oxide production (FIG. 13) and cytokines production (FIG. 14).

For nitric oxide (NO) production, macrophages were plated at $1.0\times10^6$ cells/culture in 6-well flat-bottomed tissue culture plates and incubated with glycoconjugate-treated or untreated spores. NO production by activated macrophages was studied under three conditions including (FIG. 13): A) prior to exposure (macrophages were exposed to GC3 within 9 hrs, following an infection by spores ($2.4\times10^6$/culture) within 24 hrs); B) during exposure (macrophages were exposed to GC3 coated (or treated) spores within 24-29 hrs); and following exposure (macrophages were exposed to spores within 9 hrs. GC3 was subsequently introduced and macrophage cultures were incubated within 24 hrs). Glycoconjugates concentrations were $10^{-6}$-$10^{-12}$ g/ml. Cells were incubated at 37° C. in 5% $CO_2$ for 24 hr. Supernatants (100 μl) were then assayed for NO (FIG. 13). The nitrite ion ($NO_2^-$) concentration, indicative of NO, was determined using $NaNO_2$ as a standard. Briefly, 100 μl of cell culture supernatant was mixed with an equal volume of Griess reagent [0.1% (w/v) N-(1-naphthyl)ethylenediamine dihydrochloride and 1% (w/v) sulfanilamide in 5% (v/v) phosphoric acid] (Cat. 03553-100 ML, Sigma). The samples were incubated at room temperature for 20 min and absorbance was measured at 490 nm using a Bio-Tek Ex800 plate reader.

Human macrophage production of inflammatory cytokines, including IL-6, IL-10, IL-12p70, tumor necrosis factor (TNF)-α, and IL-1B were measured using a cytokine cytometric bead array kit (BD Biosciences, CA) (FIG. 14).

Results

Peripheral blood mononuclear cells (PBMC) play a central role in inflammation in primary and/or secondary immune response against deadly infectious diseases and/or other diseases.

GalNAcα1-3 GalNAcβ-PAA-flu glycoconjugate was evaluated for the ability to modulate macrophage-mediated destruction of *Bacillus* spores during phagocytosis prior to, during, and following exposure of spores (FIG. 12). The addition of glycoconjugate GalNAcα1-3 GalNAcβ-PAA-flu resulted in almost total destruction of the spores (FIG. 12). As shown in FIG. 10, glycoconjugate GalNAcα1-3 GalNAcβ-PAA-flu facilitated the destruction of 65.5% ($p<0.01$) of spores prior to exposure, whereas the destruction of 76.4% of spores ($p<0.01$) following spores' exposure. To judge the efficacy of glycoconjugates, these were diluted to $10^{0}$-$10^{-4}$ prior to addition to spores. Results showed that 70-80% of the spores were killed at a dose of $10^{-4}$ pg/ml of glycoconjugate under prior to and during exposure conditions and almost 50% of the spores under the following exposure condition (FIG. 12).

Taken together, we observed that mammalian macrophages pre-treated with glycoconjugates destroy bacterial spores following exposure (FIG. 12). Pre-treating macrophages with plain spores followed by subsequent addition of glycoconjugates protected macrophages from spore-induced cell death (FIG. 12) and facilitate killing of the spores.

Activation of macrophages and induction of NO production was observed under three studied conditions including prior to, during exposure and following exposure (FIG. 13). Taken together, NO is antimicrobial, cytocidal agent that contribute killing of spores during phagocytosis (FIGS. 5 and 12). Furthermore, NO has pro-apoptotic effect on cells and elicit immune response.

Glycoconjugates stimulate activated macrophages and neutrophils to produce cytokines for instance IL-12p70, TNF-alpha, IL-10, IL-6, IL-LB (FIG. 14).

Apoptosis is biologically initiated by the ligation of specific receptors of the tumor necrosis receptor (TNF-R) family; these receptors include CD95/Fas/Apo-1, TNFR1, and the receptor for TRAIL; ligand binding of the trimerized receptor at the cell surface recruits intracellular adaptor molecules like FADD and TRADD in order to form the death-inducing signaling complex (DISC); autoactivation of caspase-8 is thought to follow the interaction with the DISC, and cleaves cytosolic Bid to generate a p15 fragment; this fragment translocates to mitochondria and induces the cytochrome c release, which leads to the activation of downstream caspases; the main mitochondrial feature of apoptosis is the permeabilization of the mitochondrial membrane; mitochondrial dysfunction, or permeability transition pore (PTP), can be caused by several second messengers (calcium, ceramid derivatives, and reactive oxygen species) and pro-apoptotic proteins (Bax, Bak, Bid, and caspases); this allows the escape of cytochrome c; cytochrome c induces oligomerization of Apaf-1, which recruits and activates procaspase-9 in the presence of ATP in a complex called the apoptosome; caspase-9 activates downstream caspases, including procaspase-3 that are responsible for the cytological changes characteristic of apoptosis; active caspase-3 preferentially cleaves the inhibitor of caspase-activated DNase (ICAD), and allows the translocation of the activated CAD into the nucleus, resulting in DNA degradation; therefore, the main biochemical feature of the apoptotic process is the activation of a set of caspase family proteases, and the release of mitochondrial cytochrome c to cytosol.

Spores inhibited by glycoconjugates, do not cause cell lysis, but might induce macrophage apoptosis and therefore other immune responses. Apoptosis elicit secondary immune response and activation of other immune cells. Glycoconjugate provide a protective role on cells including but not limited to macrophages and/or other cells. The presence of glycoconjugates prevents the widespread death of immune cells (FIG. 7) including but not limited to macrophages exposed to bacterial spores. Glycoconjugate have been reported to interrupt spore germination, which could contribute to macrophage efficiency (FIG. 7). Carbohydrates on the spore could serve as potential receptors for interactions with the monosaccharide moiety of the glycoconjugate, thus, lead to adhesion of other cells. Alteration of the receptors by glycoconjugates might impair spore germination. Specific carbohydrate structures expressed on pathogens and/or agents are believed to be recognized by complementary molecules expressed on the surface of interacting cells. Differences in carbohydrates expressed on exterior of spores could lead to differences in glycoconjugate effectiveness. Different glycoconjugates may exhibit different activities and this may be reflected by the differences observed in inducible NO (FIGS. 8 and 9) and/or reactive oxygen species (ROS) and/or other antimicrobial molecules production by cellular target including macrophages.

Carbohydrates are involved in recognition processes, including adhesion between cells, adhesion of cells to the extracellular matrix, and specific recognition of cells by one another. Recognition and inhibition of bacterial spores achieved by glycoconjugates are based on multivalent carbohydrate-carbohydrate interactions between carbohydrate moieties of glycoconjugate acting as ligands and carbohydrates expressed on spores and phagocytes. Glycoconjugates bound to the spores might also act as opsonins. Opsoninization promote phagocytosis, activate immune cells, and elicit primary and secondary immune response (FIGS. 11 and 14). Even highly diluted ($10^{-12}$) glycoconjugates are very effective in spore inhibition and protect cells including macrophages from cell death (FIG. 7) and promote killing of spores (FIGS. 5 and 12). Glycoconjugates can serve as chemoattractants and/or immunostimulators for macrophages and other immune cells. Glycoconjugate are having immunomodulating and immunostimulatory properties (FIGS. 8, 9 and 13). Glycoconjugate provide new targets for vaccine and/or immunomodulator and/or treatment of infections caused by spores.

Formulations: In addition, the compositions of the present invention may comprise pharmaceutically acceptable diluents, preservatives, solubilizers, emulsifiers, adjuvants and/or carriers. Such compositions include diluents of various buffer content (e.g., Tris-HCI, acetate, phosphate), pH and ionic strength; additives such as detergents and solubilizing agents (e.g., Tween 80, Polysorbate80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, and the like or into liposomes. Hyaluronic acid may also be used.

The vaccine and/or immunomodulator and/or immunotherapeutic of the present invention can be formulated and adjuvanted with a pharmaceutically acceptable carrier according to methods known and used in the art.

The adjuvants used are adjuvants conventionally used and will, in particular, be either saponin, in the case of the veterinary vaccine or immunomodulator, or advantageously chosen from the group consisting of aluminum hydroxide and squalene, in the case of the human vaccine or immunomodulator. It is preferred that the adjuvant is chosen as appropriate for use with the particular carrier used as well as the composition of the final formulation. Consideration should also be given to whether the conjugate alone will be formulated into a vaccine or whether the conjugate will be formulated into a combination vaccine. In the latter instance one should consider the buffers, adjuvants and other formulation components that will be present in the final combination vaccine.

Aluminum based adjuvants are commonly used in the art and include aluminum phosphate, aluminum hydroxide, aluminum hydroxy-phosphate and aluminum hydroxy-phosphate-sulfate. Trade names of adjuvants in common use include ADJUPHOS, MERCK ALUM and ALHYDROGEL. The conjugate can be bound to or co-precipitated with the adjuvant as desired and as appropriate for the particular adjuvant used.

Non-aluminum adjuvants can also be used if approved for use in the expected patient population. Non-aluminum adjuvants include QS21, Lipid-A and derivatives or variants thereof, Freund's complete or incomplete adjuvant, neutral liposomes, liposomes containing vaccine, microparticles and/or nanoparticles and cytokines or chemokines.

According to a particular embodiment of the invention, the immunogenic compositions can be formulated with other antigens derived from *B. anthracis* including Protective Antigen, Lethal Factor and Edema Factor, PGGA capsule polymer or peptides of PGGA and recombinant Protective Antigen or exotoxin[174] or with currently licensed vaccines. Combinations and/or conjugations have the advantages of increased patient comfort, quick response, and lower costs of administration due to the fewer inoculations required.

Pharmaceutically acceptable salts can be used for conjugation of other constituents and/or antigens and/or polymers derived from *B. anthracis* of the present invention.

Pharmaceutically acceptable salts (in form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

When formulating combination vaccines one should be mindful of the various buffers and adjuvants used with other immunogens. Some buffers may be appropriate for some immunogen-adjuvant pairs and not appropriate for others. In particular, one should assess the effects of phosphate levels on the various immunogen-adjuvant pairs to assure compatibility in the final formulation.

An antimicrobial preservative, e.g. thimerosal, optionally may be present. The immunogenic antigens of the present invention may be employed, if desired, in combination with vaccine stabilizers and vaccine adjuvants. Typical stabilizers are specific compounds, e.g. polyanions such as heparin, inositol hexasulfate, sulfated beta-cyclodextrin, less specific excipients, e.g. amino acids, sorbitol, mannitol, xylitol, glycerol, sucrose, dextrose, trehalose, and variations in solution conditions, e.g. neutral pH, high ionic strength (ca. 0.5-2.0M salts), divalent cations ($Ca^{2+}$,$Mg^{2+}$). The vaccine of the present invention may be stored under refrigeration or in lyophilized form.

Contemplated for use herein are oral solid dosage forms, which are described generally in. Solid dosage forms include tablets, capsules, pills, troches or lozenges, cachets, pellets, powders, or granules. Also, liposomal or proteinoid encapsulation may be used to formulate the present compositions. Liposomal encapsulation may be used and the liposomes may be derivatized with various polymers. A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation will include the therapeutic agent and inert ingredients which allow for protection against the stomach environment, and release of the biologically active material in the intestine.

Also contemplated for use herein are liquid dosage forms for oral administration, including pharmaceutically acceptable emulsions, solutions, suspensions, and syrups, which may contain other components including inert diluents; adjuvants, wetting agents, emulsifying and suspending agents; and sweetening, flavoring, coloring, and perfuming agents.

For oral formulations, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine, e.g., by the use of an enteric coating. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (i.e., powder), for liquid forms a soft gelatin shell may be used. The shell material of cachets could be thick starch or other edible paper. For pills, lozenges, molded tablets or tablet triturates, moist massing techniques can be used. The formulation of the material for capsule administration could also be as a powder, lightly compressed plugs, or even as tablets. These therapeutics could be prepared by compression.

One may dilute or increase the volume of the therapeutic agent with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic agent into a solid dosage form. Materials used as disintegrates include but are not limited to starch, including the commercial disintegrant based on starch, Explotab, Sodium starch glycolate, Amberlite, sodium carboxymethylcellulose, ultramylopectin, sodium alginate, gelatin, orange peel, acid carboxymethyl cellulose, natural sponge and bentonite may all be used. The disintegrants may also be insoluble cationic exchange resins. Powdered gums may be used as disintegrants and as binders, and can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the peptide (or derivative).

An antifrictional agent may be included in the formulation to prevent sticking during the formulation process. Lubricants may be used as a layer between the peptide (or derivative) and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties drug during formulation and to aid rearrangement during compression might be added. The glidants may include starch, talc, pyrogenic silica and hydrated silicoaluminate.

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylenehydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Controlled release oral formulations may used in practicing the present invention.

The therapeutic agent could be incorporated into an inert matrix which permits release by either diffusion or leaching mechanisms, e.g., gums. Slowly degenerating matrices may also be incorporated into the formulation. Some enteric coatings also have a delayed release effect.

Another form of a controlled release is by a method based on the Oros therapeutic system (AlzaCorp.), i.e. the therapeutic agent is enclosed in a semi-permeable membrane which allows water to enter and push agent out through a single small opening due to osmotic effects.

Other coatings may be used for the formulation. These include a variety of sugars which could be applied in a coating pan. The therapeutic agent could also be given in a film coated tablet and the materials used in this instance are divided into 2 groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxy-methyl cellulose, providone and the polyethylene glycols. The second group consists of the enteric materials that are commonly esters of phthalic acid. A mix of materials might be used to provide the optimum film coating. Film coating may be carried out in a pan coater or in a fluidized bed or by compression coating.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Vaccine and/or immunomodulator and/or immunostimulator: It is often observed that a primary challenge with an antigen alone, in the absence of an adjuvant, will fail to elicit a humoral or cellular immune response. Therefore the vaccines of the invention may contain adjuvants including, but not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3 hydroxyphosphoryloxy)-ethylamine, BCG (bacilli Calmette-Guerin). An adjuvant can serve as a tissue depot that slowly releases the antigen and also as a lymphoid system activator that non-specifically enhances the immune response.

Where the vaccine is intended for use in human subjects, the adjuvant should be pharmaceutically acceptable.

Administration: Pharmaceutical compositions of the present invention can be administered to a subject may be for administration by oral (solid or liquid), parenteral (intramuscular, intraperitoneal, intravenous (IV) or subcutaneous injection), transdermal (either passively or using iontophoresis or electroporation), transmucosal (nasal, vaginal, rectal, or sublingual), or inhalation routes of administration, or using bioerodible inserts and can be formulated in dosage forms appropriate for each route of administration. The doses to be administered will be determined depending on the patient for whom protection is being sought. Suitable dosing regimens are preferably determined taking into account factors well known in the art including age, weight, sex and medical condition of the subject; the route of administration; the desired effect; and the particular conjugate and formulation employed. The vaccine can be used in multi-dose formats. The compositions according to the invention may be administered alone or in combination with other vaccines, by injection or by any route conventionally used for vaccination.

In a preferred embodiment, the glycoconjugate compositions of vaccines or immunomodulators or immunotherapeutics are administered by pulmonary delivery. The composition or vaccine is delivered to the lungs of a mammal while inhaling and traverses across the lung epithelial lining to the blood stream. Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer (Mallinckrodt Inc. , St. Louis, Mo.); the Acorn II nebulizer (Marquest Medical Products, Englewood, Co.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing the therapeutic agent. Typically, each formulation is specific to the type of device employed and may involve the use of an appropriate propellant material, in addition to the usual diluents, adjuvants, surfactants and/or carriers useful in therapy. Also, the use of liposomes, microcapsules or microspheres, inclusion complexes, or other types of carriers is contemplated.

Formulations for use with a metered-dose inhaler device will generally comprise a finely divided powder containing the therapeutic agent suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing the therapeutic agent, and may also include a bulking agent, such as lactose, sorbitol, sucrose, or mannitol in amounts which facilitate dispersal of the powder from the device, e.g., 50 to 90% by weight of the formulation. The therapeutic agent should most advantageously be prepared in a particulate form with an average particle size of less than 30 nm, most preferably 0.5 to 5 nm for most effective delivery to the distal lung.

Nasal or other mucosal delivery of the therapeutic agent is also contemplated. Nasal delivery allows the passage to the blood stream directly after administering the composition to the nose, without the necessity for deposition of the product in the lung. Formulations for nasal delivery include those with dextran or cyclodextran and saponin as an adjuvant.

The composition or vaccine or immunomodulator of the present invention may be administered in conjunction with one or more additional active ingredients, pharmaceutical compositions, or vaccines. The therapeutic agents of the present invention may be administered to an animal, preferably a mammal, most preferably a human.

Dosages: Following methodologies which are well-established in the art, effective doses and toxicity of the compounds and compositions of the instant invention.

As disclosed herein, the dose of the components in the compositions of the present invention is determined to ensure that the dose administered continuously or intermittently will not exceed an amount determined after consideration of the results in test animals and the individual conditions of a subject. A specific dose naturally varies depending on the dosage procedure, the conditions of a patient or a subject animal such as age, body weight, sex, sensitivity, feed, dosage period, drugs used in combination, and seriousness of the disease. The appropriate dose and dosage times under certain conditions can be determined by the test based on the above-described indices but may be refined and ultimately decided according to the judgment of the practitioner and each patient's circumstances (age, general condition, and severity of symptoms, sex, and the like) according to standard clinical techniques.

Toxicity and therapeutic efficacy of the compositions of the invention can be determined by standard pharmaceutical procedures in cell culture, experimental animals, e.g., by determining the % of spore killing. LC50 (the lethal concentration to 50% of the population), the LD50 (the dose lethal to 50% of the population), and the ED50 (the dose therapeutically effective in 50% of the population) can be used for identification of efficacy. The dose ratio between therapeutic and toxic effects is the therapeutic index and it can be expressed as the ratio ED50/LD50. Compositions that exhibit large therapeutic indices are preferred. The therapeutically effective doses of in humans lay preferably within a range of circulating concentrations that include the ED50 with little or no toxicity. The dosage can vary within this range depending upon the dosage form employed and the route of administration utilized. Ideally, a single dose of each drug should be used daily.

The dosage of a glycoconjugate compound will depend on route of administration, number of bacteria, number of administrations and will vary according to the species to be protected. Compounds should persist in the host for extended periods of time, usually weeks, to enhance the effectiveness of the immunizing effect by continuous stimulation of the host immune system until the host immune system has cleared all the organisms. In view of the fact that the non-virulence does not depend on any host cellular function, compound is expected to be non-virulent and non-toxic even in immunodeficient hosts.

In one embodiment of the present invention where glycoconjugates are administered to a subject to treat or prevent bacterial spores infection prior to, during, and following exposure, the amount will be determined based e.g., on the in vitro colony forming units (CFU) of the bacterial strain infecting, or at risk of infecting, and the route of infection of the host. Alternatively, the LD50 can be used. Published LD50 for anthrax by the parenteral route range from less than 10 spores for a guinea pig through $3\times10^3$ for the rhesus monkey, $10^6$ for the rat, $10^9$ for the pig and $5\times10^1$ for the dog. Minimum infectious dose (MID) estimates are only rarely available, but an aerosol MID for sheep of 35,000 spores has been recorded.

In one embodiment, the glycoconjugate immunostimulator of the present invention may be administered parenterally against *B. anthracis* in a range from about $1\times10^6$ to $1\times10^1$, preferably within a range from about $1\times10^7$ to about $2\text{-}6\times10^9$. In a preferred embodiment, the cells are administered parenterally, optionally in conjunction with an adjuvant, e.g., saponin.

Compounds: glycoconjugate compounds will be administered to a subject in a range from about 0.00001 mg/μL of blood or equal to 2-8% of total leukocytes of healthy adults (according to the formed elements of blood of healthy adults or 5,000-9,000 leukocytes/μL prior to exposure, preferably, from about 0.000001-0.000002 g/ml of blood during exposure, and more preferably, from about 0.000003-0.000005 g/ml following exposure. For example, for administration for the evaluation of immunostimulation in a murine macrophages model, about 0.000001 g/$10^6$ macrophages, may be administered.

Referring now to FIGS. 5-14, results according to embodiments of the present invention are shown.

FIG. 5 shows glycoconjugates (GC) facilitate spore destruction by murine macrophages. *B. cereus* spores were treated for 1 hr either with Galα1-3 GalNAcα-PAA-flu (GC1) or GalNAcα1-3 GalNAcβ-PAA-flu (GC3) at studied concentrations and then added to macrophage cultures (A). The same number of untreated spores was added to other macrophage cultures (B) or to culture medium with the absence of macrophages (C). Cultures were then plated for bacterial growth (CFU), $p < 0.01$. In FIG. 5D, these results were expressed as mean percent bacterial killing of untreated spores and spores treated with glycoconjugates GC1 and GC3. These results are representative of triplicate experiments.

FIG. 6 shows glycoconjugates protected murine macrophages from spore-induced damage. *B. cereus* spores were treated for 1 hr with the glycoconjugates and then added, as described in FIG. 5, to macrophage cultures. After 24 hr, macrophage LDH was assayed in macrophages exposed to untreated spores or to treated spores. These results are representative of duplicate experiments.

FIG. 7 shows glycoconjugates protected murine macrophage viability after exposure to *Bacillus* spores. Macrophages were exposed to treated (A) or untreated spores (B) and stained for viability with trypan blue 24 hr later. Live macrophages are transparent (A), dead macrophages are stained black/gray (B). The viability for macrophages exposed to untreated and treated spores are shown (C). These results are representative of triplicate experiments.

FIG. 8 shows glycoconjugates stimulated murine macrophage nitric oxide (NO) production. Macrophage cultures were exposed to untreated and treated spores. After 24 hr, macrophage NO production was measured by the Griess assay. These results are representative of triplicate experiments FIG. 9 shows glycoconjugates stimulated murine macrophage nitric oxide (NO) production prior to, during and following exposure. Macrophage cultures were exposed to untreated and treated spores prior to, during and following exposure. Three conditions were applied prior to exposure (macrophages were exposed to GCs within 9 hrs, following an infection by spores ($1.0\times10^6$/culture) within 24 hrs); during exposure (macrophages were exposed to GCs coated spores within 24-29 hrs); and following exposure (macrophages were exposed to spores within 9 hrs. After 24 hr, macrophage NO production was measured by the Griess assay. These results are representative of triplicate experiments.

FIG. 10 shows Comet assay based on tail vs. head of GC1 (A) and GC3 treated spores (B), macrophages only (C), macrophages exposure untreated spore (D), macrophages exposed to glycoconjugates only either GC1 (E) or GC3 (F).

FIG. 11 shows glycoconjugates stimulated cytokines production during phagocytosis. Macrophage cultures were exposed to untreated and GC1 and GC3 treated spores. After 24 hr, macrophage cytokines production was measured using the BD™ Cytometric Bead Array (CBA). IL-12p70 (A); TNF-alpha (B), INF gamma (C); MCP-1 (D); IL-6 (E); IL-10 (F) are shown. Glycoconjugates concentrations $100\text{-}10^{-12}$ were used. These results are representative of duplicate experiments.

FIG. 12 shows glycoconjugates facilitate spore destruction using human macrophages isolated from peripheral blood mononuclear cells. Three conditions were applied prior to exposure (macrophages were exposed to GCs within 9 hrs, following an infection by spores ($2.4\times10^6$/culture) within 24 hrs); during exposure (macrophages were exposed to GCs coated spores within 24-29 hrs); and following exposure (macrophages were exposed to spores within 9 hrs. GCs were subsequently introduced within 24 hrs). Glycoconjugates concentrations were $10^0\text{-}10^{-4}$ g/ml. Cultures were then plated for bacterial growth (CFU), $p<0.01$. These results are expressed as mean percent bacterial killing of untreated spores and spores treated with glycoconjugate GC1 or GC3. $LC_{50}$ can be identified for GC#3 for following exposure condition. These results are representative of duplicate experiments.

FIG. 13 shows glycoconjugates stimulate human macrophage nitric oxide (NO) production. Macrophage cultures were exposed to untreated spores, as well as to spores GC3-treated with concentration ($10^0\text{-}10^{-4}$ g/ml). After 24 hrs, macrophage NO production was measured by the Griess assay. Results are representative of duplicate experiments.

FIG. 14 shows glycoconjugates influence cytokines production by human macrophages during phagocytosis. Three conditions were applied prior to exposure (macrophages were exposed to GCs within 9 hrs, following an infection by spores ($2.4\times10^6$/culture) within 24 hrs); during exposure (macrophages were exposed to GCs coated spores within 24-29 hrs); and following exposure (macrophages were exposed to spores within 9 hrs. GCs were subsequently introduced within 24 hrs). Glycoconjugates concentrations were $10^0\text{-}10^{-4}$ g/ml. Supernatant were assayed using the BD™ Cytometric Bead Array (CBA). IL-12p70 (A); TNF-alpha (B), IL-10 (C); IL-6 (D); IL-1B (E) are shown. Glycoconjugates concentrations $100\text{-}10^{-12}$ were used. These results are representative of duplicate experiments.

The present invention relates to the use of glycoconjugates and/or carbohydrate polymers comprising carbohydrates and a polymer moiety as a single compound and/or cocktail of glycoconjugates as prophylactic or therapeutic or immunotherapeutic composition for preventing and/or immunomodulating and/or immunostimulating and/or treating a disease and their pathological conditions associated with bacterial spores and/or their vegetative cells and/or toxins in humans and animal life-stock. An aspect of this invention is a vaccine or immuno-prophylactic or immunostimulant against a disease, toxicity or death caused by *B. anthracis* spores prior to, during, or following exposure to *B. anthracis* spores. The vaccine and immunotherapeutic of this invention are administered to a subject in a manner appropriate for the induction in the subject of an immune response against *B. anthracis* spores and prevent macrophages and/or other immune cells from spores and/or toxins of *B. anthracis-induced* cell death and activate immune cells. According to the invention, glycoconjugates, which have shown to bind to, recognize, distinguish, and inhibit *Bacillus* spores, are capable of modulating interactions between macrophages and bacterial spores of *B. cereus* group during phagocytosis, prior to exposure and/or during exposure and following exposure of bacterial spores including but not limited to *B. anthracis*. In the presence of glycoconjugates, however, macrophages efficiently killed bacterial spores. Glycoconjugates are effective, even at very low concentrations. Glycoconjugates have a protective influence, sparing macrophages from spore-induced cell death. Very low glycoconjugate concentrations prevent macrophage cell death, as shown by lactate dehydrogenase (LDH) release and trypan blue assays. Increased levels of inducible nitric oxide production by macrophages in presence of glycoconjugates suggested that glycoconjugates provide an activation signal to macrophages. Glycoconjugates promote killing of *Bacillus* spores by blocking spore-induced phagocyte cell death, while increasing phagocyte activation level and production of antimicrobial and cytocidal agents such as NO and inflammatory cytokines. Without activation, phagocyte cells (amoeba, macrophage, neutrophil) were ineffective at killing *Bacillus* spores. The glycoconjugates suggest a novel approach for prevention a prophylactic vaccine, immunomodulation, immunostimulation, and treatment of infection with organisms, such as *B. anthracis* and/or other members of *B. cereus* group. Furthermore, glycoconjugates facilitate functions and activate macrophages and/or other peripheral blood mononuclear cells (PBMC) prior to exposure, and/or during exposure, and/or following exposure of bacterial spores and/or their vegetative cells and/or toxins in humans and/or in animal life-stock. All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCES

[1] Philips ML, Nudelman E, Gaeta FC, Perez M, Singhal AK, Hakomori S, Paulson JC, "ELAM-1 mediates cell adhesion by recognition of a carbohydrate ligand, sialyl-Lex," Science 1990; 250: 1130-1132.

[2] Liener I. E., Sharon, N., Goldstein, I. J. eds The Lectins: Properties, functions and applications in biology and medicine. New York: Academic. 1986.

[3] Zaman, Handbook of Medical Parasitology, $2^{nd}$ edition. 1989.

[4] Schmidt, Foundations of Parasitology. $5^{th}$ edition 1996.

[5] Black J. G. Microbiology: Principles and Explorations. Sixth Edition. John Wiley & Sons, Inc. Publishing. 2005, pp. 450-453.

[6] van der Laan, L. J., S.R. Ruuls, K. S. Weber, I. J. Lodder, E .A. Dopp, and C. D. Dijkstra. Macrophage phagocytosis of myelin in vitro determined by flow cytometry: phagocytosis is mediated by CR3 and induces production of tumor necrosis factor-alpha and nitric oxide. J. Neuroimmunol. 1996; 70: 145-152.

[7] Koenigsknecht, J. and G. Landreth. Microglial phagocytosis of fibrillar beta-amyloid through a betal integrin-dependent mechanism. J. Neurosci. 2004; 24: 9838-9846.

[8] Patel, M., J. Morrow, F.R. Maxfield, O.K. Strickland, S. Greenberg, and I. Tabas. 2003. The cytoplasmic domain of the low density lipoprotein (LDL) receptor-related protein, but not that of the LDL receptor, triggers phagocytosis. J. Biol. Chem. 275:44799-44807.

[9] Rotrosen, D. and J. I. Gallin. 1987. Disorders of phagocyte function. Annu. Rev. Immunol. 5:127-150.

[10] Kelleher M., Bacic A., E. Handman. Identification of a Macrophage-Binding Determinant on Lipophosphoglycan from Leishmania Major Promastigotes. Proceedings of the National Academy of Sciences, Vol. 89, p6-10, 1992 (Abstract).

[11] Witting A., Muller P., Herrmann A., Kettenmann H., Nolte C. Phagocytic Clearance of Apoptotic Neuron by Microglia/Brain Macrophages in Vitro. Journal of Neurochemistry, Vol. 75, p1060, 2000 (Abstract).

[12] Bogwald J., I. Gouda, J. Hoffman, O. Larm, R. Larsson & R. Seljelid. Stimulatory Effect of Immobilized Glycans on Macrophages in Vitro. Scandinavian J. of Immunology 20(4):355-360, 1984.

[13] Florian H. Pilsczek, Anne Nicholson-Weller, and Lonita Ghiran. Phgocytosis of *Salmonella montevideo* by Human Neutrophils: Immune Adherence Increases Phagocytosis, whereas the Bacterial Surface Determines the Route of Intracellular Processing. Journal of Infectious Diseases, 192, p200-209, 2005.

[14] Rajagopalan P, E Dournon, J L Vilde and J J Pocidalo. Direct activation of human monocyte-derived macrophages by a bacterial glycoprotein extract inhibits the intracellular multiplication of virulent Legionella pneumophila serogroup I. Infect Immun. 55(9): 2234-2239, 1987.

[15] Richard R. Schmidt. New approaches to glycoconjugate synthesis. Pure & Appl. Chem., Vol. 70, No. 2, p397-402, 1998.

[16] GlycoTech Inc., Rockville, MD. Instruction manual. 2004.

[17] Chow, C.W., G.P. Downey, and S. Grinstein. 2004. Measurement of phagocytosis and phagosomal maturation, p. 15.7.1-15.7.33. In J .S . Boni-facino, M. Dasso, J. Lippincott- Schwartz, J.B. Harford, and K. M. Yamada (Eds.), Current Protocols in Cell Biology. John Wiley & Sons, New York.

[18] Kawano, Y., Fukata, Y., Oshiro, N., Amano, M., Nakamura, T., Ito, M., Matsumura, F., Inagaki, M. and Kaibuchi, K. Phosphorylation of myosin-binding subunit (MBS) of myosin phosphatase by Rho-kinase in vivo. J. Cell Biol. 147, 1023-1037, 1999.

[19] Tarasenko 0., Burton E., Soderberg L., Alusta P. Glycoconjugates and their role in phagocytosis and destruction of *B. cereus spores. Polymeric Materials: Science and Engineering* 2007, 96, 946-947.

[20] Tarasenko 0., Burton E., Desikan S., Bush J., Alusta P. Glycoconjugates enhanced phagocytosis of B. cereus spores using *Dictyostelium discoideum* as a model. *Polymeric Materials: Science and Engineering* 2007, 96, 82-83.

What is claimed is:

1. A method of preparing a phagocyte for killing a spore produced by a bacterium comprising the step of providing an effective amount of a glycan activating the phagocyte for phagolysosome formation.

2. The method of claim 1, said glycan comprising a carbohydrate moiety selected from the group consisting of Galβ1-3GalNAcα, Galβ1-3GalNAcβ, Fucα1-3GlcNAcβ, Fucα1-4GlcNAc, Fucβ1-3GlcNAcβ, Galβ1-4GalNAcα, Galβ1-4Glcβ, GalNAcα1-3GalNAcβ, GalNAcα1-3GalNAcα, GlcNAcβ1-3Galβ, GlcNAcβ1-4GlcNAcβ, Galα1-4GlcNAcβ, GalNAcβ1-3GalNAcβ, Glcα1-4Glcβ, Galα1-2Galβ, Neu5Acα2-6GalNAcα, Galα1-6Glcβ, Galβ1-2Galβ, Neu5Acα2-3Gal, Neu5Acα2-6Galβ, Neu5Gcα2-6GalNAcα, Neu5Acβ2-6GalNAcαand Neu5Acα2-3GalNAcαas a single compound.

3. The method of claim 1, wherein said step occurs in a body of a human or a non-human animal before exposure to the spore.

4. The method of claim 1, wherein said step occurs in a body of a human or a non-human animal either during or following exposure to the spore.

5. The method of claim 4, wherein the spore is present in an extracellular space or tissue fluid in the body of the human or the non-human animal.

6. The method of claim 1, wherein the glycan is immunogenic, or an immunomodulator or immunostimulator.

7. The method of claim 1, wherein the glycan increases adherence of the spore to the phagocyte.

8. The method of claim 1, wherein the glycan increases production of an antimicrobial agent.

9. The method of claim 1, wherein the glycan is a carbohydrate unit covalently linked with another type of chemical constituent.

10. The method of claim 1, wherein the glycan comprises a plurality of carbohydrate moieties in one molecule or in a plurality of different molecules, and combinations thereof.

11. The method of claim 8, wherein the antimicrobial agent comprises nitric oxide and said glycan increases the production of a cytocidal agent.

12. The method of claim 1, wherein the phagocyte is selected from the group consisting of monocyte, macrophage, neutrophil and amoeba.

13. The method of claim 1, wherein the killing of spores removes environmental contamination and the phagocyte is an amoeba *Dictyostelium discoideum.*

14. The method of claim 1, wherein the bacterium is selected from the group consisting of genus *Clostridium* and genus *Bacillus.*

15. The method of claim 14, wherein the bacterium is selected from the group consisting of *Bacillus cereus* and *Bacillus anthracis.*

16. A method of enhancing phagocytosis of spores produced by a bacterium, comprising the step of subjecting the spores to an effective amount of a glycoconjugate to facilitate ingestion of the spores and formation of phagosomes by the phagocytes.

17. The method of claim 16, wherein said glycoconjugate activates the phagosomes.

18. The method of claim 17, wherein said glycoconjugate increases production of antimicrobial and cytocidal agents.

19. The method of claim 18, wherein the antimicrobials and cytocidal agents comprise NO and inflammatory cytokines.

20. The method of claim 16, wherein the spores are present in a body of a human or a non-human animal.

21. The method of claim 16, wherein the human or the non-human animal is at an early stage of infection by the spores.

22. The method of claim 16, wherein the spores are present in an extracellular space or tissue fluid in the body of the human or the non-human animal.

23. The method of claim 16, wherein the glycoconjugate is immunogenic, or an immunomodulator or immunostimulator.

24. The method of claim 16, wherein the glycoconjugate increases adherence of the spores to the phagocytes.

25. The method of claim 24, wherein the glycoconjugate facilitates phagosome-lysosome fusion in the phagocytes.

26. The method of claim 16, wherein the glycoconjugate is selected from the group consisting of glycan, glycoprotein, glycolipid, and any combinations thereof.

27. The method of claim 16, wherein the glycoconjugate is a carbohydrate unit covalently linked with another type of chemical constituent.

28. The method of claim 16, wherein the glycoconjugate comprises a carbohydrate moiety selected from the group consisting of Galβ1-3GalNAcα, Galβ1-3GalNAcβ, Fucα1-3GlcNAcβ, Fucα1-4GlcNAc, Fucβ1-3GlcNAcβ,Galβ1-4GalNAcα, Galβ1-4Glcβ, GalNAcα1-3GalNAcβ, GalNAcα1-3GalNAcα, GlcNAcβ1-3Galβ, GlcNAcβ1-4GlcNAcβ, Galα1-4GlcNAcβ, GalNAcβ1-3GalNAcβ, Glcα1-4Glcβ, Galα1-2Galβ, Neu5Acα2-6GalNAcα, Galα1-6Glcβ, Galβ1-2Galβ, Neu5Acα2-3Gal, Neu5Acα2-6Galβ, Neu5Gcα2-6GalNAcα, Neu5Acβ2-6GalNAcα, and Neu5Acα2-3GalNAcαas a single compound.

29. The method of claim 28, wherein the glycoconjugate comprises a plurality of said carbohydrate moieties in one molecule or in a plurality of different molecules, and combinations thereof.

30. The method of claim 16, wherein the phagocyte is selected from the group consisting of monocyte, macrophage, neutrophil and amoeba.

31. The method of claim 16, wherein said step of subjecting the spores to an effective amount of a glycoconjugate removes environmental contamination and the phagocyte is an amoeba *Dictyostelium discoideum.*

32. The method of claim 16, wherein the bacterium is selected from the group consisting of genus *Clostridium* and genus *Bacillus.*

33. The method of claim 32, wherein the bacterium is selected from the group consisting of *Bacillus cereus* and *Bacillus anthracis.*

34. A method of enhancing phagocytosis of spores produced by a bacterium comprising the step of subjecting phagocytes to an effective amount of a glycan activating the phagocytes for phagolvsosome formation.

35. The method of claim 34, wherein the glycan is a carbohydrate unit covalently linked with another type of chemical constituent.

36. The method of claim 34, wherein the glycan comprises a carbohydrate moiety selected from the group consisting of Galβ1-3GalNAcα, Galβ1-3GalNAcβ, Fucα1-3GlcNAcβ, Fucα1-4GlcNAc, Fucβ1-3GlcNAcβ, Galβ1-4GalNAcα, Galβ1-4Glcβ, GalNAcα1-3GalNAcβ, GalNAcα1-3GalNAcα, GlcNAcβ1-3Galβ, GlcNAcβ1-4GlcNAcβ, Galα1-4GlcNAcβ, GalNAcβ1-3GalNAcβ, Glcα1-4Glcβ, Galα1-2Galβ, Neu5Acα2-6GalNAcα, Galα1-6Glcβ, Galβ1-2Galβ, Neu5Acα2-3Gal, Neu5Acα2-6Galβ, Neu5Gcα2-6GalNAcα, Neu5Acβ2-6GalNAcαand Neu5Acα2-3GalNAcαas a single compound.

37. The method of claim 34, wherein the human or non-human animal is at an early stage of infection by the spores.

38. The method of claim 37, wherein the spores are present in an extracellular space or tissue fluid in the body of the human or non-human animal.

* * * * *